United States Patent
Baxter et al.

(10) Patent No.: US 6,201,024 B1
(45) Date of Patent: Mar. 13, 2001

(54) ADAMANTANE DERIVATIVES

(75) Inventors: Andrew Baxter, Wymeswold; Thomas McInally, Loughborough; Michael Mortimore, West Bridgford; David Cladingboel, Mountsorrel, all of (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/230,478

(22) PCT Filed: Dec. 1, 1998

(86) PCT No.: PCT/SE98/02188

§ 371 Date: Jan. 26, 1999

§ 102(e) Date: Jan. 26, 1999

(87) PCT Pub. No.: WO99/29661

PCT Pub. Date: Jun. 17, 1999

(30) Foreign Application Priority Data

Dec. 5, 1997 (SE) ..................................... 9704544

(51) Int. Cl.$^7$ ...................... A61K 31/166; A61K 31/404; A61K 31/44; C07C 233/65; C07D 213/82
(52) U.S. Cl. .......................... 514/617; 564/183; 546/285; 546/276.4; 548/469; 548/361.1; 544/335; 514/345; 514/347; 514/349; 514/403; 514/415; 514/256
(58) Field of Search ..................................... 514/617, 256, 514/345, 347, 349, 350, 403, 415; 564/183; 546/276.4, 285; 548/361.1, 469; 554/335

(56) References Cited

U.S. PATENT DOCUMENTS

| | | | |
|---|---|---|---|
| 3,464,998 | 9/1969 | Krimmel . | |
| 3,732,305 | * 5/1973 | Bauer et al. | ...................... 260/564 R |
| 3,789,072 | 1/1974 | Bernstein | ......................... 260/557 B |

FOREIGN PATENT DOCUMENTS

| | | |
|---|---|---|
| 0 395 093 | 10/1990 | (EP) . |
| 0 564 924 A2 | 10/1993 | (EP) . |
| 0 564 924 A3 | 10/1993 | (EP) . |
| 95/04720 | 2/1995 | (WO) . |
| 95/30647 | 11/1995 | (WO) . |

OTHER PUBLICATIONS

Narayanan, V.L., "Adamantyl Analogs of 2'–(3–Dimethylaminopropylthio) . . . ," Journal of Medicinal Chemistry, vol. 15, No. 11 (1972).
STN Int'l, accession No.: 1975:592744, "Antiviral Agents", Kreutzberger et al.
STN In'l, accession No: 1974:26871, "Synthesis and biological activity . . ."Danilenko et al.
STN Int'l , accession No: 1968:402562, "Synthesis of adamantane derivatives . . . " Sasaki et al.
STN Int'l, accession No: 1975:3853, "Aliphatic acid amide . . . " Kreutzberger et al.
Syamala et al, "Modification of Photochemical Reactivity by Cyclodextrin . . . ," Tetrahedron, vol. 44, No. 23, pp. 7234 to 7242 (1988).
STN Int'l, accession No. 1977:89560, Danilenko et al, "Synthesis and biological activity . . . " (1976), 10(8), 51–3.
STN Int'l, accession No. 1996:34490, Kalindjian et al, "The synthesis of a radioligand with high potency . . . " Bioorg. Med. Chem. Lett., vol. 6, No. 10, pp. 1171–1174 (1996).
STN Int'l, accession No. 1997:390174, Gibson et al, "Incorproation of conformationally constrained . . . " Bioorg. Med. Chem. Lett., vol. 7, No. 10, pp. 1289–1292 (1997).

* cited by examiner

Primary Examiner—C. S. Aulakh
(74) Attorney, Agent, or Firm—Nixon & Vanderhye

(57) ABSTRACT

The invention provides adamantane derivatives, a process for their preparation, pharmaceutical compositions containing them, a process for preparing the pharmaceutical compositions, and their use in therapy.

9 Claims, No Drawings

ADAMANTANE DERIVATIVES

The present invention relates to adamantane derivatives, a process for their preparation, pharmaceutical compositions containing them, a process for preparing the pharmaceutical compositions, and their use in therapy.

Adamantane derivatives are known in the art, e.g. from WO 95/04720 for use as gastrin and cholecystokinin receptor ligands, from Chem. Abs. (1977), Volume 86, No. 13 (86: 89560d) for use as analgesics, and from U.S. Pat. No. 3,464,998 as antibiotics.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and L-selectin shedding (lymphocytes). $P2X_7$ receptors are also located on antigen-presenting cells (APC), keratinocytes, salivary acinar cells (parotid cells) and hepatocytes.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

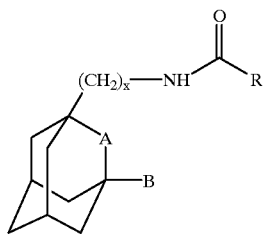

(I)

wherein x represents 1 or 2; A represents a group $CH_2$ or an oxygen atom;

B represents a hydrogen or halogen atom (e.g. fluorine, bromine, iodine or especially chlorine);

R represents a phenyl, pyridyl, indolyl, indazolyl, pyrimidinyl or thiophenyl group, each of which may be optionally substituted by one or more substituents independently selected from a halogen atom or an amino, cyano, carboxyl, hydroxyl, nitro, $C_1$–$C_6$-alkyl, halo-$C_1$–$C_6$-alkyl, —N($R^1$)—C(=O)—$R^2$, —C(O)N$R^3R^4$, —N$R^5R^6$, $C_3$–$C_8$-cycloalkyl, 3- to 8-membered heterocyclyl, $C_3$–$C_8$-cycloalkyloxy, $C_1$–$C_6$-alkylcarbonyl, $C_1$–$C_6$-alkoxycarbonyl, $C_1$–C6-alkylsulphinyl or $C_1$–$C_6$-alkylsulphonyl group, or a $C_1$–$C_6$-alkoxy, $C_1$–$C_6$-alkylamino, phenoxy, benzyl, $C_1$–$C_6$-alkylthio or phenylthio group optionally substituted by one or more substituents independently selected from a halogen atom or an amino, cyano, carboxyl, hydroxyl,nitro, 1-pyrrolidinyl, 1-piperidinyl, $C_1$–$C_6$-alkyl, $C_1$–$C_6$-alkoxy, (di)$C_1$–$C_6$-alkylamino, halo-$C_1$–$C_6$-alkyl, $C_1$–$C_6$-alkoxycarbonyl or one of the following groups:

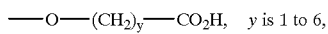

—O—(CH$_2$)$_y$—CO$_2$H,  y is 1 to 6,

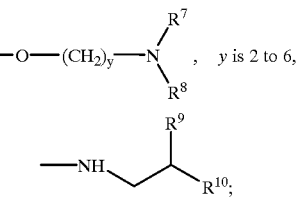

$R^1$ represents a hydrogen atom or a $C_1$–$C_6$-alkyl or $C_3$–$C_8$-cycloalkyl group;

$R^2$ represents a $C_1$–$C_6$-alkyl or $C_3$–$C_8$-cycloalkyl group;

$R^3$ and $R^4$ each independently represent a hydrogen atom or a $C_1$–$C_6$-alkyl or $C_3$–$C_8$-cycloalkyl group;

$R^5$ represents a hydrogen atom or a $C_1$–$C_6$-alkyl or $C_3$–$C_8$-cycloalkyl group;

$R^6$ represents a $C_3$–$C_8$-cycloalkyl group and, additionally, a $C_1$–$C_6$-alkyl group when R is not a hydrogen atom;

$R^7$ represents a hydrogen atom or a $C_1$–$C_6$-alkyl or $C_3$–$C_8$-cycloalkyl group;

$R^8$ represents a $C_1$–$C_6$-alkyl or $C_3$–$C_8$-cycloalkyl group;

$R^9$ represents a hydrogen atom or a hydroxyl group; and $R^{10}$ represents a hydrogen atom or a phenyl or imidazolyl group;

with the provisos that R does not represent an unsubstituted pyridyl group when A represents a group $CH_2$ and B represents a hydrogen atom, and that when R represents a substituted phenyl, indolyl or indazolyl group, the substituent or substituents present do not comprise an amido, carboxyl, (di) $C_1$–$C_6$-alkylamido or $C_1$–$C_6$-alkoxycarbonyl group in an ortho position; or a pharmaceutically acceptable salt or solvate thereof.

In the context of the present specification, unless otherwise indicated, an alkyl substituent or alkyl moiety in a substituent group may be linear or branched. Furthermore, the (cyclo)alkyl moieties in a dialkylamino, dicycloalkylamino, dialkylamido or dicycloalkylamido substituent group may be the same or different. A 3- to 8-membered heterocyclyl group should be understood to mean an aliphatic heterocyclic ring system containing a single heteroatom selected from nitrogen, oxygen or sulphur. The term "in an ortho position" defines the ring position on the phenyl, indolyl or indazolyl ring of R which is adjacent to the point of attachment of the amide linking group to R, e.g., as illustrated in the formula below where the asterisks define the "ortho position":

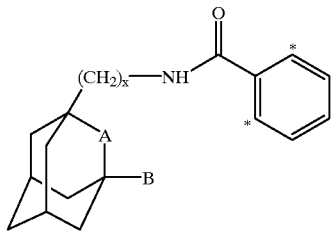

Preferably, R represents a phenyl, pyridyl, indolyl, indazolyl, pyrimidinyl or thiophenyl group, each of which may be optionally substituted by one, two, three or four substituents independently selected from a halogen atom (e.g. fluorine, chlorine, bromine or iodine) or an amino, cyano, carboxyl, hydroxyl, nitro, $C_1$–$C_6$-alkyl (e.g. methyl, ethyl, propyl, butyl, pentyl or hexyl), halo-$C_1$–$C_6$-alkyl (e.g. trifluoromethyl), —N($R^1$)—C(=O)—$R^2$, —C(O)N$R^3R^4$, —N$R^5R^6$, $C_3$–$C_8$-cycloalkyl (e.g. cyclopropyl, cyclobutyl, cyclopentyl or cyclohexyl), 3- to 8-membered heterocyclyl (e.g. aziridinyl, pyrrolidinyl, piperidinyl), $C_3$–$C_8$-cycloalkyloxy (e.g. cyclopropyloxy, cyclobutyloxy, cyclopentyloxy or cyclohexyloxy), $C_1$–$C_6$-alkylcarbonyl (e.g. methyl-, ethyl-, propyl-, butyl-,pentyl- or hexylcarbonyl), $C_1$–$C_6$-alkoxycarbonyl (e.g. methoxy-, ethoxy-, propoxy-, butoxy-, pentoxy- or hexoxycarbonyl), $C_1$–$C_6$-aLlcylsulphinyl (e.g. methyl-, ethyl-, propyl-, butyl-, pentyl- or hexylsulphinyl), or $C_1$–$C_6$-alkylsulphonyl (e.g. methyl-, ethyl-, propyl-, butyl-, pentyl- or hexylsulphonyl) group, or a $C_1$–$C_6$-alkoxy (e.g. methoxy, ethoxy, propoxy, butoxy, pentoxy or hexoxy), $C_1$–$C_6$-alkylamino (e.g. methyl-, ethyl-, propyl-, butyl-, pentyl- or hexylamnino), phenoxy, benzyl, $C_1$–$C_6$-alkylthio (e.g. methyl-, ethyl-, propyl-, butyl-, pentyl- or hexylthio) or phenylthio group optionally substituted by one, two, three or four substituents independently selected from a halogen atom (e.g. fluorine, chlorine, bromine or iodine) or an amino, cyano, carboxyl, hydroxyl, nitro, 1-pyrrolidinyl, 1-piperidinyl, $C_1$–$C_6$-alkyl (e.g. methyl, ethyl, propyl, butyl,pentyl or hexyl), $C_1$–$C_6$-alkoxy (e.g. methoxy, ethoxy, propoxy, butoxy, pentoxy or hexoxy), $(di)C_1$–$C_6$-alkylamino (e.g. dimethylamnino or diethylamino), halo-$C_1$–$C_6$-alkyl (e.g. trifluoromethyl), $C_1$–$C_6$-alkoxycarbonyl (e.g. methoxy-, ethoxy-,propoxy-, butoxy-, tert-butoxy-, pentoxy- or hexoxycarbonyl) or one of the following groups:

$$—O—(CH_2)_y—CO_2H, \quad y \text{ is 1 to 6,}$$

$$—O—(CH_2)_y—N\begin{matrix}R^7\\R^8\end{matrix}, \quad y \text{ is 2 to 6,}$$

$$—NH\diagup\diagdown\begin{matrix}R^9\\R^{10}\end{matrix}.$$

More preferably R represents a phenyl, pyridyl or indolyl group, each of which may be optionally substituted by one or two substituents independently selected from a fluorine, chlorine, bromine or iodine atom or an amino, hydroxyl, nitro, aziridinyl, pyrrolidinyl, $C_1$–$C_4$-alkyl (particularly methyl), trifluoromethyl, —$NR^5R^6$, $C_1$–$C_4$-alkylsulphinyl (particularly methylsulphinyl) or $C_1$–$C_4$-alkylsulphonyl (particularly methylsulphonyl) group, or a $C_1$–$C_4$-alkoxy (especially $C_1$–$C_2$-alkoxy), $C_1$–$C_4$-alkylamino (especially $C_1$–$C_2$-alkylamino), benzyl, $C_1$–$C_4$-alkylthio (especially $C_1$–$C_2$-alkylthio) or phenylthio group optionally substituted by one or two substituents independently selected from a halogen atom (especially chlorine atom) or an amino, cyano, carboxyl, hydroxyl, 1-pyrrolidinyl, 1-piperidinyl, methyl, methoxy, dimethylamino, $C_1$–$C_4$-alkoxycarbonyl (especially tert-butoxycarbonyl) or one of the following groups:

$$—O—(CH_2)_y—CO_2H, \quad y \text{ is 1 to 3,}$$

$$—O—(CH_2)_y—N\begin{matrix}CH_3\\CH_3\end{matrix}, \quad y \text{ is 2 to 3,}$$

$$—NH\diagup\diagdown\begin{matrix}R^9\\R^{10}\end{matrix}.$$

It is preferred that $R^1$ represents a hydrogen atom or a $C_1$–$C_4$-alkyl (e.g. methyl, ethyl, propyl or butyl) or $C_3$–$C_6$-cycloalkyl (e.g. cyclopentyl or cyclohexyl) group.

Preferably $R^2$ represents a $C_1$–$C_4$-alkyl (e.g. methyl, ethyl, propyl or butyl) or $C_3$–$C_6$-cycloalkyl (e.g. cyclopentyl or cyclohexyl) group.

Preferably, $R^3$ and $R^4$ each independently represent a hydrogen atom or a $C_1$–$C_4$-alkyl (e.g. methyl, ethyl, propyl or butyl) or $C_3$–$C_6$-cycloalkyl (e.g. cyclopentyl or cyclohexyl) group.

It is preferred that $R^5$ represents a hydrogen atom or a $C_1$–$C_4$-alyl (e.g. methyl, ethyl, propyl or butyl, especially methyl) or $C_3$–$C_6$-cycloalkyl (e.g. cyclopentyl or cyclohexyl) group and that $R^6$ represents a $C_3$–$C_6$-cycloalkyl (e.g. cyclopentyl orcyclohexyl) group and, additionally, a $C_1$–$C_4$-alkyl (e.g. methyl, ethyl, propyl or butyl, especially methyl) group when R is not a hydrogen atom.

It is preferred that $R^7$ represents a hydrogen atom or a $C_1$–$C_4$-alkyl (e.g. methyl, ethyl, propyl or butyl) or $C_3$–$C_6$-cycloalkyl (e.g. cyclopentyl or cyclohexyl) group and is especially a methyl group.

Preferably $R^8$ represents a $C_1$–$C_4$-alkyl (e.g. methyl, ethyl, propyl or butyl) or $C_3$–$C_6$-cycloalkyl (e.g. cyclopentyl or cyclohexyl) group and is especially a methyl group.

Preferred compounds of the invention include:

2,4-Dichloro-N-(tricyclo[3.3.1.1$^{3,7}$]dec-1-methyl)-benzamide, 3,5-Dichloro-N-(tricyclo[3.3.1.1$^{3,7}$]dec-1-methyl)-benzamide, 2-Chloro-N-(tricyclo[3.3.1.1$^{3,7}$]dec-1-methyl)-benzamide, 2,6-Dichloro-N-(tricyclo[3.3.1.1$^{3,7}$]dec-1-methyl)-benzamide, 2-Methoxy-N-(tricyclo[3.3.1.1$^{3,7}$]dec-1-methyl)-benzamide, 2-Methyl-N-(tricyclo[3.3.1.1$^{3,7}$]dec-1-methyl)-benzamide, 2-Bromo-N-(tricyclo[3.3.1.1$^{3,7}$]dec-1-methyl)-benzamide, 2-Iodo-N-(tricyclo[3.3.1.1$^{3,7}$]dec-1-methyl)-benzamide, 2-Nitro-N-(tricyclo[3.3.1.1$^{3,7}$]dec-1-methyl)-benzamide, 2,6-Dimethoxy-N-(tricyclo[3.3.1.1$^{3,7}$]dec-1-methyl)-benzamide, 2-(Trifluoromethyl)-N-(tricyclo[3.3.1.1$^{3,7}$]dec-1-methyl)-benzamide, 2,6-Difluoro-N-(tricyclo[3.3.1.1$^{3,7}$]dec-1-methyl)-benzarnide, 2-(Trifluoromethyl)-6-flouro-N-(tricyclo[3.3.1.1$^{3,7}$]dec-1-methyl)-benzamide, 2-Amino-6-chloro-N-(tricyclo[3.3.1.1$^{3,7}$]dec-1-methyl)-benzamide, 2-Chloro4-nitro-N-(tricyclo[3.3.1.1$^{3,7}$]dec-1-methyl)-benzamide, 2-(2-Cyanophenylthio)-N-(tricyclo[3.3.1.1$^{3,7}$]dec-1-methyl)-benzamide, 2-(4-Methylphenylthio)-N-(tricyclo[3.3.1.1$^{3,7}$]dec-1-methyl)-3-pyridine carboxamide, 2-(Methylthio)-N-(tricyclo[3.3.1.1$^{3,7}$]dec-1-methyl)-benzamide, 2-(Methylthio)-N-(tricyclo[3.3.1.1$^{3,7}$]dec-1-methyl)-3-pyridine carboxamide, 3-Chloro-N-(tricyclo[3.3.1.1$^{3,7}$]dec-1-methyl)-benzaride, 2,3-Dichloro-N-(tricyclo[3.3.1.1$^{3,7}$]dec-1-methyl)-benzamide, 2,5-Dimethyl-N-(tricyclo[3.3.1.1$^{3,7}$dec-1-methyl)-benzamide, 2-(Phenylmethyl)-N-(tricyclo[3.3.1.1$^{3,7}$]dec-1-methyl)-benzamide, 2-(2-(N,N-Dimethylamino)ethyloxy)-N-(tricyclo[3.3.1.1$^{3,7}$]dec-1-methyl)-benzamide, hydrochloride, 2-[[(Tricyclo[3.3.1.1$^{3,7}$]dec-1-ylmethyl)amino]carbonyl]phenyl-1-oxyacetic acid, 1,1-dimethylethyl ester, 2-[[(Tricyclo[3.3.1.1³,⁷]dec-1-ylmethyl)amnino]carbonyl] phenyl-1-oxyacetic acid,
2-(Methylsulphoxide)-N-(tricyclo[3.3.1.1³,⁷]dec-1-methyl)-3-pyridine carboxamide,
N-(tricyclo[3.3.1.1³,⁷]dec-1-methyl)-5-indole carboxamide,
2-Amino-6-chloro-N-(2-[tricyclo[3.3.1.1³,⁷]dec-1-yl]ethyl) benzamide,
2-(2-Methylsulphonyl)-N-(tricyclo[3.3.1.1³,⁷]dec-1-ylmethyl)-3-pyridine carboxamide,
2-(2-Aminoethylthio)-N-(tricyclo[3.3.1.1³,⁷]dec-1-ylmethyl)-3-pyridine carboxamide, trifluoroacetate,
2-(2-(N,N-Dimethylamino)ethylamino)-N-(tricyclo[3.3.1.1³,⁷]dec-1-ylmethyl)-3-pyridine carboxamide, dihydrochloride,
2-(2-(Pyrrolidin-1-ylethylamino)-N-(tricyclo[3.3.1 1³,⁷]dec-1-ylmethyl)-3-pyridine carboxamide, dihydrochloride,
2-(Methylamino)-N-(tricyclo[3.3.1.1³,⁷]dec-1-ylmethyl)-3-pyridine carboxamide, dihydrochloride,
2-(Dimethylamino)-N-(tricyclo[3.3.1.1³,⁷]dec-1-ylmethyl)-3-pyridine carboxamide, hydrochloride,
2-(Pyrrolidin-1-yl)-N-(tricyclo[3.3.1.1³,⁷dec-1-ylmethyl)-3-pyridine carboxamide, dihydrochloride,
2-(2,5-Dimethoxyphenylthio)-N-(tricyclo[3.3.1.1³,⁷]dec-1-ylmethyl)-3-pyridine carboxamide,
2-Chloro-5-methylthio-N-(tricyclo[3.3.1.1³,⁷]dec-1-ylmethyl)benzamide,
2-(2-(N,N-Dimethylamino)ethylthio)-N-(tricyclo[3.3.1.1³,⁷]dec-1-ylmethyl)benzamide,
2-(4-Methoxyphenylthio)-N-(tricyclo[3.3.1.1³,⁷]dec-1-ylmethyl)-3-pyridine carboxamide,
2-Chloro-3-fluoro-N-(tricyclo[3.3.1.1³,⁷]dec-1-ylmethyl)benzamide,
2-Bromo-5-fluoro-N-(tricyclo[3.3.1.1³,⁷]dec-1-ylmethyl)-benzanide,
2-Chloro-5-fluoro-N-(tricyclo[3.3.1.1³,⁷]dec-1-ylmethyl)-benzamide,
2-(2,5-Dihydroxyphenylthio)-N-(tricyclo[3.3.1.1³,⁷]dec-1-ylmethyl)-3-pyridine carboxamide,
3-[[(Tricyclo[3.3.1.1³,⁷]dec-1-ylmethyl)amino]carbonyl] pyridyl-2-thioacetic acid,
(2-Chloro-6-methyl)-N-(tricyclo[3.3.1.1³,⁷]dec-1-ylmethyl)-3-pyridine carboxamide,
3-[[(Tricyclo[3.3.1.1³,⁷]dec-1-ylmethyl)amino]carbonyl] pyridyl-2-(4phenylthio)oxyacetic acid,
2-(4-(3-N,N-dimethylamino)propyloxyphenylthio)-N-(tricyclo[3.3.1.1³,⁷]dec-1-ylmethyl)-3-pyridine carboxamide, dihydrochloride,
(2-Methylthio-6-methyl)-N-(tricyclo[3.3.1.1³,⁷]dec-1-ylmethyl)-3-pyridine carboxamide,
2-[[(Tricyclo[3.3.1.1³,⁷]dec-1-ylmethyl)arnino]carbonyl] phenyl-1-oxybutyric acid,
2-Chloro-5-hydroxy-N-(tricyclo[3.3.1.1³,⁷]dec-1-ylmethyl) benzamide,
2-Chloro-3-nitro-N-(tricyclo[3.3.1.1³,⁷]dec-1-ylmethyl) benzamide,
2-Chloro-5-nitro-N-(tricyclo[3.3.1.1³,⁷]dec-1-ylmethyl)-benzamide,
3-Amino-2-chloro-N-(tricyclo[3.3.1.1³,⁷]dec-1-ylmethyl)-benzamide,
5-Amino-2-chloro-N-(tricyclo[3.3.1.1³,⁷]dec-1-ylmethyl) benzamide,
2-Chloro-3-(N,N-dimethylamino)ethylamino-N-(tricyclo[3.3.1.1³,⁷]dec-1-ylmethyl)-benzamide,
2-Chloro-5-(N,N-dimethylamino)ethylamino-N-(tricyclo[3.3.1.1³,⁷]dec-1-ylmethyl)-benzamide,
2-Chloro-5-(N,N-dimethylamino)ethylthio-N-(tricyclo[3.3.1.1³,⁷]dec-1 -ylmethyl)-benzamide, fumarate,
2-Chloro-3-hydroxy-N-(tricyclo[3.3.1.1³,⁷]dec-1-ylmethyl) benzamide,
2-Chloro-5-(N,N-dimethylamino)ethyloxy-N-(tricyclo[3.3.1.1³,⁷]dec-1-ylmethyl)-benzamide,
2,5-Dichloro-N-(tricyclo[3.3.1.1³,⁷]dec-1-ylmethyl) benzamide,
2-Chloro-5-methylamino-N-(tricyclo[3.3.1.1³,⁷]dec-1-ylmethyl)benzamide,
2-Chloro-5-(2-chloroethyl)amino-N-(tricyclo[3.3.1.1³,⁷] dec-1-ylmethyl)benzamide,
5-Aziridin-1-yl-2-chloro-N-(tricyclo[3.3.1.1³,⁷]dec-1-ylmethyl)benzamide,
2-Methyl-3,5-dinitro-N-(tricyclo[3.3 1.1³,⁷]dec-1-ylmethyl)-benzamide,
3,5-Diamino-2-methyl-N-(tricyclo[3.3.1.1³,⁷]dec-1-ylmethyl)benzamide,
3,5-Dimethoxy-2-methyl-N-(tricyclo[3.3.1.1³,⁷]dec-1-ylmethyl)-benzamide,
3,5-Dimethoxy-N-(tricyclo[3.3.1.1³,⁷]dec-1-ylmethyl) benzamide,
5-(N-(2-Hydroxy-2-phenylethyl)-2-aminoethyl)amino-2-chloro-N-(tricyclo[3.3.1.1³,⁷]dec-1-ylmethyl)-benzamide,
2-Chloro-5-(2-(piperidin-1-ylethylamino)-N-(tricyclo[3.3.1.1³,⁷]dec-1-ylmethyl)-benzamide, hydrochloride,
5-(N-(2-Hydroxyethyl)-2-aminoethyl)amino-2-chloro-N-(tricyclo[3.3.1.1³,⁷]dec-1-ylmethyl)benzamide, dihydrochloride,
2-Chloro-N-(2-[tricyclo[3.3.1.1³,⁷]dec-1-yl]ethyl)-benzamide,
2,3-Dichloro-N-(2-[tricyclo[3.3.1.1³,⁷]dec-1-yl]ethyl)-benzamide,
5-Amino-2-chloro-N-(2-[tricyclo[3.3.1.1³,⁷]dec-1-yl]ethyl) benzamide,
2,5-Dimethyl-N-(2-[tricyclo[3.3.1.1³,⁷]dec-1-yl]ethyl)-benzamide,
2-Chloro-N-(3chloro-tricyclo[3.3.1.1³,⁷]dec-1-ylmethyl) benzamide,
2-Chloro-3-(N-(2-[imidazoyl4-yl]ethyl)-2-aminoethyl) amino-N-(tricyclo[3.3.1.1³,⁷]dec-1-ylmethyl)-benzamide,
2,5-Dimethyl-N-(3-chloro-tricyclo[3.3.1.1³,⁷]dec-1ylmethyl)benzamide,
3,5-Dimethoxy-2-methyl-N-(3-chloro-tricyclo[3.3.1.1³,⁷] dec-1ylmethyl)benzamide, and
2-Chloro-5-iodo-N-(tricyclo[3.3.1.1³,⁷]dec-1-ylmethyl)-benzamide.

The present invention further provides a process for the preparation of a compound of formula (I) as defined above which comprises reacting a compound of general formula

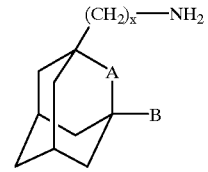

(II)

wherein x, A and B are as defined in formula (I), with a compound of general formula

(III)

wherein R is as defined in formula (I) and L is a leaving group such as a halogen atom (e.g. chlorine), an imidazole group or an urea; and optionally forming a pharmaceutically acceptable salt or solvate thereof.

The process may conveniently be carried out in a solvent (e.g. dichloromethane, tetrahydrofuran, dioxan or dimethylformamide) and optionally in the presence of a base (e.g. triethylamine or diisopropylethylarnine). The process is conveniently operated at a temperature in the range from 0 to 100° C., preferably in the range from 10 to 80° C., and especially at ambient temperature (20° C.).

The compounds of formula (II) and (III) are known compounds or may be prepared by processes analogous to those known in the art.

It will be appreciated by those skilled in the art that in the process of the present invention certain functional groups such as hydroxyl or amino groups in the intermediate compounds may need to be protected by protecting groups. Thus, the final stage in the preparation of the compounds of formula (I) may involve the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity. They are therefore indicated as pharmaceuticals for use in the treatment or prevention of rheumatoid arthritis, osteoarthritis, psoriasis, allergic dermatitis, asthma, hyperresponsiveness of the airway, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, bum injury, ischaemic heart disease, stroke and varicose veins.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will be further understood by reference to the following illustrative examples in which the terms MS, NMR and DMSO denote respectively mass spectrometry, nuclear magnetic resonance and dimethylsulphoxide.

EXAMPLE 1

2,4-Dichloro-N-(tricyclo[3.3.1.1$^{3,7}$]dec-1-methyl)-benzamide

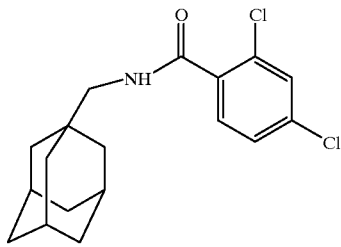

To a solution of 1-adamantanemethylamine (0.1 ml) in dichloromethane (5 ml) were added triethylarnine (0.16 ml) and 2,4-dichlorobenzoyl chloride (0.118 g). The resulting reaction mixture was stirred for 2 hours and then diluted with diethyl ether. Thereafter, an organic phase was separated and washed with dilute hydrochloric acid followed by sodium hydrogencarbonate solution and then brine. The organic phase was subsequently dried over sodium sulphate ($Na_2SO_4$) and concentrated under reduced pressure to give the title compound as a white solid (0.17 g).

Melting point: 180–182° C.

MS (APCI+ve) 338/340/342 (M+H)$^+$ $^1$H NMR (DMSO-d$_6$) δ 8.57 (1H, t), 7.67 (1H, d), 7.48 (1H, dd), 7.42 (1H, d), 2.93 (2H, d), 1.94 (3H, s), 1.66 (3H, d), 1.60 (3H, d), 1.51 (6H, d)

EXAMPLE 2

3,5-Dichloro-N-(tricyclo[3.3.1.1$^{3,7}$]dec-1-methyl)-benzamide

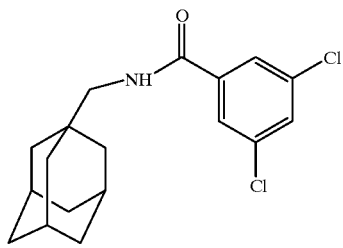

Prepared according to the method of Example 1 from 1-adamantanemethylamine (0.1 ml) and 3,5-dichlorobenzoyl chloride (0.118 g) to give the title compound as a white solid (0.18 g).

Melting point: 197–198° C.

MS (APCI+ve) 338/340/342 (M+H)$^+$ $^1$H NMR (DMSO-d$_6$) δ 8.51 (1H, t), 7.87 (2H, d), 7.81 (1H, dd), 2.98 (2H, d), 1.93 (3H, s), 1.65 (3H, d), 1.60 (3H, d), 1.49 (6H, d)

EXAMPLE 3

2-Chloro-N-(tricyclo[3.3.1.1$^{3,7}$]dec-1-methyl)-benzamide

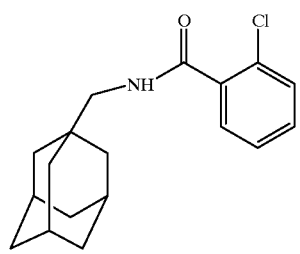

Prepared according to the method of Example 1 from 1-adamantanemethylamine (0.1 ml) and 2-chlorobenzoyl chloride (0.099 g) to give the title compound as a white solid (0.16 g).

Melting point: 148–152° C.

MS (APCI+ve) 304/306 (M+H)$^+$ $^1$H NMR (DMSO-d$_6$) δ 8.33 (1H, t), 7.48 (1H, d), 7.45-7.37 (3H, m), 2.93 (2H, d), 1.94 (3H, s), 1.66 (3H, d), 1.60 (3H, d), 1.52 (6H, d)

EXAMPLE 4

2,6-Dichloro-N-(tricyclo[3.3.1.1$^{3,7}$]dec-1-methyl)-benzamide

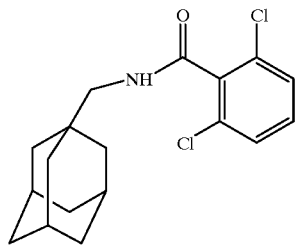

Prepared according to the method of Example 1 from 1-adamantanemethylamine (0.1 ml) and 2,6-dichlorobenzoyl chloride (0.118 g) to give the title compound as a white solid (0.18 g).

Melting point: 246–247° C.

MS (APCI+ve) 338/340/342 (M+H)$^+$ $^1$H NMR (DMSO-d$_6$) δ 8.54 (1H, t), 7.49 (2H, dd), 7.41 (1H, dt), 2.93 (2H, d), 1.94 (3H, s), 1.67 (3H, d), 1.59 (3H, d), 1.54 (6H, d)

EXAMPLE 5

2-Methoxy-N-(tricyclo[3.3.1.1$^{3,7}$]dec-1-methyl)-benzamide

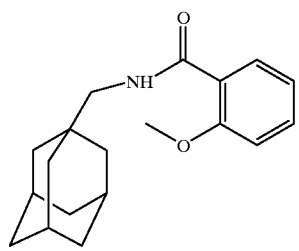

Prepared according to the method of Example 1 from 1-adamantanemethylamine (0.1 ml) and 2-methoxybenzoyl chloride (0.087 g) to give the title compound as a gum (0.16 g).

MS (APCI+ve) 300 (M+H)$^+$ $^1$H NMR (DMSO-d$_6$) δ 8.01 (1H, t), 7.70 (1H, dd), 7.46 (1H, dt), 7.14 (1H, dd), 7.03 (1H, dt), 3.90 (3H, s), 3.00 (2H, d), 1.95 (3H, s), 1.67 (3H, d), 1.61 (3H, d), 1.51 (6H, d)

EXAMPLE 6

2-Methyl-N-(tricyclo[3.3.1.1$^{3,7}$]dec-1-methyl)-benzamide

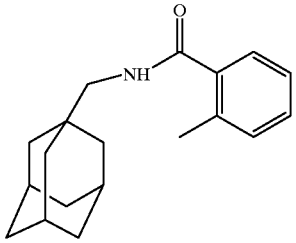

Prepared according to the method of Example 1 from 1-adamantanemethylamine (0.1 ml) and 2-methylbenzoyl chloride (0.078 g) to give the title compound as a white solid (0.13 g).

Meting point 150–152° C.

MS (APCI+ve) 284 (M+H)$^+$ $^1$H NMR (DMSO-d$_6$) δ 8.12 (1H, t), 7.31 (2H, m), 7.23 (2H, m), 2.94 (2H, d), 2.33 (3H, s), 1.94 (3H, s), 1.66 (3H, d), 1.61 (3H, d), 1.50 (6H, d)

EXAMPLE 7

2-Bromo-N-(tricyclo[3.3.1.1$^{3,7}$]dec-1-methyl)-benzamide

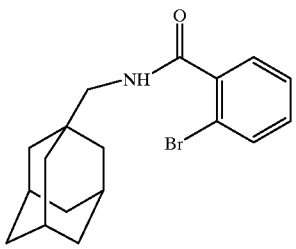

Prepared according to the method of Example 1 from 1-adamantanemethylamine (0.1 ml) and 2-bromobenzoyl chloride (0.111 g) to give the title compound as a white solid (0.17 g).

Melting point: 157–159° C.

MS (APCI+ve) 348/350 (M+H)$^+$ $^1$H NMR (DMSO-d$_6$) δ 8.31 (1H, t), 7.64 (1H, dd), 7.45-7.31 (3H, m), 2.92 (2H, d), 1.94 (3H, s), 1.66 (3H, d), 1.62 (3H, d), 1.53 (6H, d)

EXAMPLE 8

2-Iodo-N(tricyclo[3.3.1.1$^{3,7}$]dec-1-methyl)-benzamide

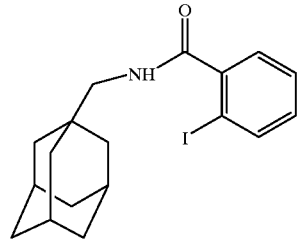

Prepared according to the method of Example 1 from 1-adamantanemethylamine (0.1 ml) and 2-iodobenzoyl chloride (0.134 g) to give the title compound as a white solid (0.18 g).

Melting point: 194–195° C.

MS (APCI+ve) 396 (M+H)$^+$ $^1$H NMR (DMSO-d$_6$) δ 8.25 (1H, t), 7.86 (1H, dd), 7.43 (1H, dt), 7.29 (1H, dd), 7.15 (1H, dt), 2.92 (2H, d), 1.94 (3H, s), 1.65 (6H, m), 1.55 (6H, d)

EXAMPLE 9

2-Nitro-N-(tricyclo[3.3.1.1$^{3,7}$]dec-1-methyl)-benzamide

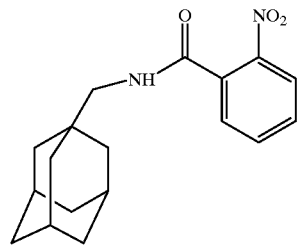

Prepared according to the method of Example 1 from 1-adamantanemethylaImine (0.1 ml) and 2-nitrobenzoyl chloride (0.094 g) to give the title compound as a pale yellow solid (0.13 g).

Melting point: >250° C.

MS (APCI+ve) 315 (M+H)$^+$ $^1$H NMR (DMSO-d$_6$) δ 8.54 (1H, t), 8.02 (1H, dd), 7.78 (1H, dt), 7.67 (1H, dt), 7.59 (1H, dd), 2.93 (2H, d), 1.94 (3H, s), 1.67 (3H, d), 1.62 (3H, d), 1.52 (6H, d)

EXAMPLE 10

2,6-Dimethoxy-N-(tricyclo[3.3.1.1³,⁷]dec-1-methyl)-benzamide

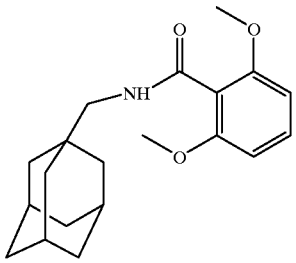

Prepared according to the method of Example 1 from 1-adamantanemethylamine (0.1 ml) and 2,6-dimethoxybenzoyl chloride (0.102 g) to give the title compound as a white solid (0.13 g).

Melting point: 185–186° C.

MS (APCI+ve) 330 (M+H)$^+$ $^1$H NMR (DMSO-d$_6$) δ 7.90 (1H, t), 7.26 (1H, t), 6.65 (2H, d), 3.72 (6H, s), 2.84 (2H, d), 1.93 (3H, s), 1.66 (3H, d), 1.60 (3H, d), 1.50 (6H, d)

EXAMPLE 11

2-(Trifluoromethyl)-N-(tricyclo[3.3.1.1³,⁷]dec-1-methyl)-benzamide

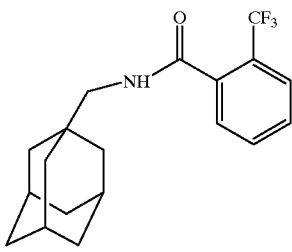

Prepared according to the method of Example 1 from 1-adamantanemethylamine (0.1 ml) and 2-(trifluoromethyl) benzoyl chloride (0.090 g) to give the title compound as a white solid (0.14 g).

Melting point: 165–167° C.

MS (APCI+ve) 338 (M+H)$^+$ $^1$H NMR (DMSO-d$_6$) δ 8.36 (1H, t), 7.76 (1H, d), 7.72 (1H, t), 7.63 (1H, t), 7.51 (1H, d), 2.93 (2H, d), 1.94 (3H, s), 1.67 (3H, d), 1.61 (3H, d), 1.51 (6H, d)

EXAMPLE 12

2,6-Difluoro-N-(tricyclo[3.3.1.1³,⁷]dec-1-methyl)-benzamide

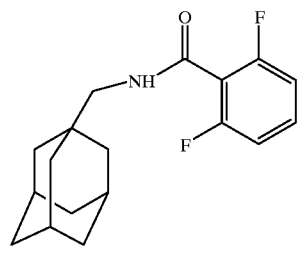

Prepared according to the method of Example 1 from 1-adamantanemethylamine (0.1 ml) and 2,6-difluorobenzoyl chloride (0.090 g) to give the title compound as a white solid (0.14 g).

Melting point: 162–163° C.

MS (APCI+ve) 306 (M+H)$^+$ $^1$H NMR (DMSO-d$_6$) δ 8.58 (1H, t), 7.50 (1H, m), 7.14 (2H, m), 2.95 (2H, d), 1.94 (3H, s), 1.67 (3H, d), 1.59 (3H, d), 1.50 (6H, d)

EXAMPLE 13

2-(Trifluoromethyl)-6-flouro-N-(tricyclo[3.3.1.1³,⁷] dec-1-methyl)-benzamide

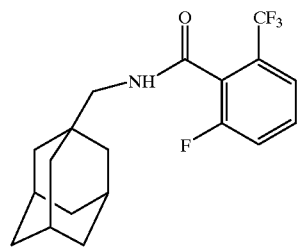

Prepared according to the method of Example 1 from 1-adamantanemethylamine (0.1 ml) and 2-(trifluoromethyl)-6-fluorobenzoyl chloride (0.115 g) to give the title compound as a white solid (0.18 g).

Melting point: 151–153° C.

MS (APCI+ve) 356 (M+H)$^+$ $^1$H NMR (DMSO-d$_6$) δ 8.57 (1H, t), 7.68-7.59 (3H, m), 2.95 (2H, d), 1.94 (3H, s), 1.66 (3H, d), 1.59 (3H, d), 1.50 (6H, d)

EXAMPLE 14

2-Amino-6-chloro-N-(tricyclo[3.3.1.1$^{3,7}$]dec-1-methyl)-benzamide

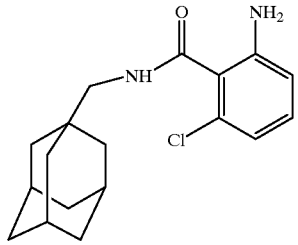

To a solution of 2-amino-6-chlorobenzoic acid (0.087 g) in N,N-dimethylformamide (1.5 ml) was added carbonyldi-imidazole (0.082 g). The resulting reaction mixture was stirred for 2.5 hours and then 1-adamantanemethylamine (0.1 ml) was added. Stirring was continued overnight. On the following day, the reaction mixture was partitioned between ethyl acetate and water and the organic layer was separated, washed with water and brine and then dried over sodium sulphate (Na$_2$SO$_4$). The organic layer was subsequently concentrated under reduced pressure to give a residue which was purified by silica gel chromatography (eluting with 3–10% methanol in dichloromethane) to yield the title compound as a white solid (0.072 g).

Melting point: 182–183° C.

MS (APCI+ve) 319/321 (M+H)$^{30}$ $^1$H NMR (DMSO-d$_6$) δ 8.31 (1H, t), 7.02 (1H, t), 6.63 (1H, d), 6.59 (1H, d), 5.12 (2H, s), 2.93 (2H, d), 1.93 (3H, s), 1.65 (3H, d), 1.60 (3H, d), 1.53 (6H, d)

EXAMPLE 15

2-Chloro4-nitro-N-(tricyclo[3.3.1.1$^{3,7}$]dec-1-methyl)-benzamide

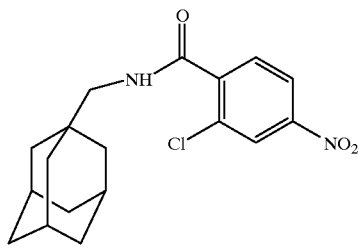

Prepared according to the method of Example 14 from 1-adamantanemethylamine (0.1 ml) and 2-chloro-nitrobenzoic acid (0.102 g) to give the title compound as a yellow solid (0.10 g).

Melting point: 154–155° C.

MS (APCI+ve) 348/350 (M+H)$^+$ $^1$H NMR (DMSO-d$_6$) δ 8.59 (1H, t), 8.34 (1H, d), 8.23 (1H, d), 7.69 (1H, d), 2.96 (2H, d), 1.95 (3H, s), 1.67 (3H, d), 1.61 (3H, d), 1.53 (6H, d)

EXAMPLE 16

2-(2-Cyanophenylthio)-N-(tricyclo[3.3.1.1$^{3,7}$]dec-1-methyl)-benzamide

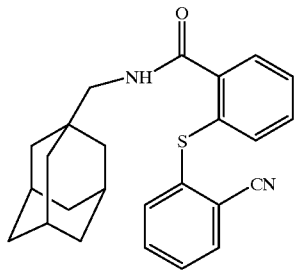

Prepared according to the method of Example 14 from 1-adamantanemethylamine (0.1 ml) and 2-(2-cyanophenylthio)benzoic acid (0.144 g) to give the title compound as a white foam (0.19 g).

Melting point: 62–65° C.

MS (APCI+ve) 403 (M+H)$^{30}$ $^1$H NMR (DMSO-d$_6$) δ 8.34 (1H, t), 7.89 (1H d), 7.81 (1H, d), 7.55 (1H, m),7.44 (3H,m 7.25 (1H, d), 7.18 (1H, m), 2.92 (2H, d), 1.88 (3H, s), 1.62 (3H, d), 1.54 (3H, d), 1.41 (6H, d)

EXAMPLE 17

2-(4-Methylphenylthio)-N-(tricydo[3.3.1.1$^{3,7}$]dec-1-methyl)-3-pyridine carboxamide

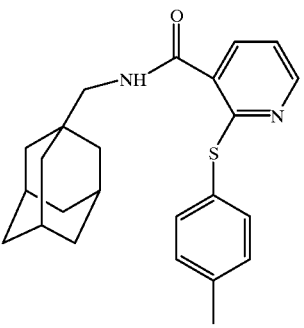

Prepared according to the method of Example 14 from 1-adamantanemethylamine (0.1 ml) and 2-(4-methylphenylthio)pyridine-3-carboxylic acid (0.138 g) to give the title compound as a white solid (0.21 g).

Melting point: 166–169° C.

MS (APCI+ve) 393 (M+H)$^{30}$ $^1$H NMR (DMSO-d$_6$) δ 8.46 (1H, t), 8.31 (1H d), 7.77 (1H, d), 7.34 (2H, d), 7.20 (3H, m), 2.97 (2H, d), 2.33 (3H, s), 1.95 (3H, s), 1.67 (3H, d), 1.61 (3H, d), 1.55 (6H, d)

EXAMPLE 18

2-(Methylthio)-N-(tricyclo[3.3.1.1$^{3,7}$]dec-1-methyl)-benzamide

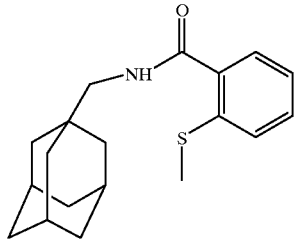

Prepared according to the method of Example 14 from 1-adamantanemethylamine (0.1 ml) and 2-methylthiobenzoic acid (0.095 g) to give the title compound as a waxy white solid (0.15 g).

Melting point: 171–172° C.

MS (APCI+ve) 316 (M+H)$^{30}$ $^1$H NMR (DMSO-d$_6$) δ 8.16 (1H, t), 7.4-7.3 (3H, m), 7.18 (1H, dt), 2.91 (2H, d), 2.40 (3H, s), 1.94 (3H, s), 1.67 (3H, d), 1.60 (3H, d), 1.52 (6H, d)

EXAMPLE 19

2-(Methylthio)-N-(tricyclo[3.3.1.1$^{3,7}$]dec-1-methyl)-3-pyridine carboxamide

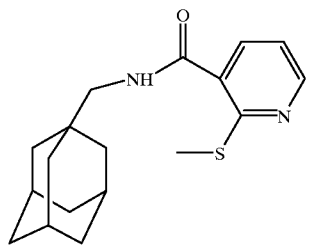

Prepared according to the method of Example 14 from 1-adamantanemethylamine (0.1 ml) and 2-methylthiopyridine-3-carboxylic acid (0.095 g) to give the title compound as a white solid (0.17 g).

Melting point: 118–120° C.

MS (APCI+ve) 317 (M+H)$^{30}$ $^1$H NMR (DMSO-d$_6$) δ 8.51 (1H, dd), 8.34 (1H, t), 7.72 (1H, dd), 7.17 (1H, m), 2.93 (2H, d), 2.44 (3H, s), 1.94 (3H, s), 1.67 (3H, d), 1.61 (3H, d), 1.52 (6H, d)

EXAMPLE 20

3-Chloro-N-(tricyclo[3.3.1.1$^{3,7}$]dec-1-methyl)-benzamide

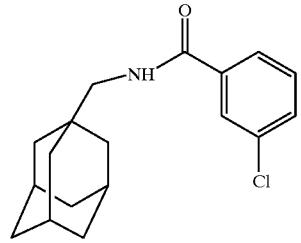

Prepared according to the method of Example 1 from 1-adamantanemethylamine (0.1 ml) and 3-chlorobenzoyl chloride (0.090 g) to give the title compound as a white solid (0.10 g).

Melting point: 125–126° C.

MS (APCI+ve) 304/306 (M+H)$^{30}$ $^1$H NMR (DMSO-d$_6$) δ 8.41 (1H, t), 7.89 (1H, t), 7.81 (1H, dt), 7.59 (1H, ddd), 7.50 (1H, t), 2.98 (2H, d), 1.93 (3H, s), 1.65 (3H, d), 1.60 (3H, d), 1.49 (6H, d)

EXAMPLE 21

2,3-Dichloro-N-(tricyclo[3.3.1.1$^{3,7}$]dec-1-methyl)benzamide

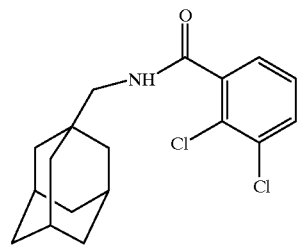

Prepared according to the method of Example 1 from 1-adamantanemethylamine (0.1 ml) and 2,3-dichlorobenzoyl chloride (0.104 g) to give the title compound as a white solid (0.10 g).

Melting point: 175–176° C.

MS (APCI+ve) 338/340/342 (M+H)$^{30}$ $^1$H NMR (DMSO-d$_6$) δ 8.42 (1H, t), 7.68 (1H, dd), 7.41 (1H, t), 7.36 (1H, ddd), 2.93 (2H, d), 1.94 (3H, s), 1.67 (3H, d), 1.60 (3H, d), 1.52 (6H, d)

EXAMPLE 22

2,5-Dimethyl-N-(tricyclo[3.3.1.1$^{3,7}$]dec-1-methyl)-benzamide

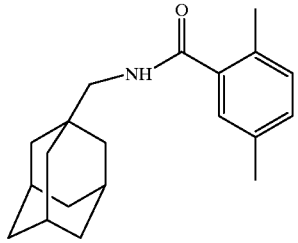

To a solution of 2,5-dimethylbenzoic acid (0.12 g) in dichoromethane (2 ml) was added a mixed solution of 4-dimethylaminopyridine and 1-(3-methylaminopropyl)-3-ethylcarbodiimide hydrochloride (2 ml of 0.41M solution in dichloromethane). The reaction mixture was stirred for 0.5 hour and then a solution of 1-adamantanemethylamine (2 ml of a 0.45M solution in dichloromethane) was added. Stirring was continued at room temperature overnight. On the following day, the reaction mixture was washed with dilute hydrochloric acid, water and brine, dried over sodium sulphate ($Na_2SO_4$) and concentrated under reduced pressure to leave a yellow solid that was triturated under diethyl ether to give the title compound as a white solid (0.12 g).

Melting point: 153–154° C.

MS (APCI+ve) 298 (M+H)$^+$ $^1$H NMR (DMSO-d$_6$) δ 8.07 (1H, t), 7.13 (3H, m), 2.92 (2H, d), 2.28 (6H, s), 1.82 (3H, s), 1.63 (6H, dd), 1.50 (6H, d)

EXAMPLE 23

2-(Phenylmethyl)-N-(tricycio[3.3.1.1$^{3,7}$]dec-1-methyl)-benzamide

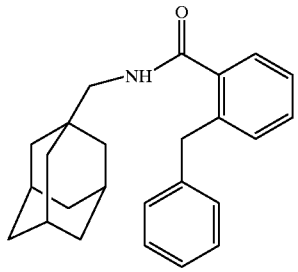

Prepared according to the method of Example 22 from 1-adamantanemethylamine (0.15 g) and 2-phenylmethylbenzoic acid (0.17 g) to give the title compound as an off-white solid (0.15 g).

Melting point: 156–157° C.

MS (APCI+ve) 360 (M+H)$^+$ $^1$H NMR (DMSO-d$_6$) δ 8.20 (1H, t), 7.36-7.11 (9H, m), 4.10 (2H, s), 2.93 (2H, d), 1.89 (3H, s), 1.60 (6H, dd), 1.46 (6H, d)

EXAMPLE 24

2-(2-(N,N-Dimethylamino)ethyloxy)-N-(tricyclo [3.3.1.1$^{3,7}$]dec-1 -methyl)-benzamide, hydrochloride

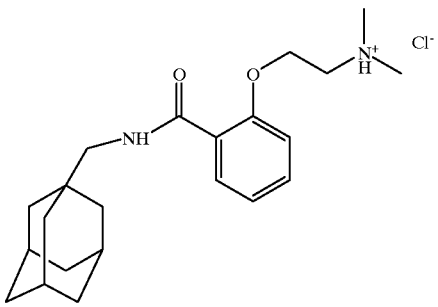

a) 2-Hydroxy- N-(tricyclo[3.3.1.1$^{3,7}$]dec-1-methyl)-benzamide

To a solution of 1-adamantanemethylamine (0.2 ml) in dichloromethane (4 ml) were added triethylamine (0.32 ml) and 2-acetoxybenzoyl chloride (0.224 g). The reaction mixture was stirred at room temperature for 1.5 hours and then diluted with methanol. Potassium carbonate (0.50 g) was added and the resulting suspension was stirred at room temperature for 2 hours before being partitioned between diethyl ether and dilute hydrochloric acid. An organic phase was separated, washed with brine, and then dried over sodium sulphate ($Na_2SO_4$). Concentration of the organic phase under reduced pressure yielded a yellow solid that was triturated under isohexanes to give the sub-title compound as a white solid (0.27 g).

MS (APCI+ve) 286 (M+H)$^{30}$ $^1$H NMR (DMSO-d$_6$) δ 12.52 (1H, s), 8.64 (1H, t), 7.89 (1H, dd), 7.39 (1H, dt), 6.91 (2H, m), 3.03 (2H, d), 1.94 (3H, s), 1.66 (3H, d), 1.60 (3H, d), 1.50 (6H, d)

b) 2-(2-(N,N-Dimethylamino)ethyloxy)-N-(tricyclo [3.3.1.1$^{3,7}$]dec-1-methyl)-benzamide, hydrochloride To a solution of 2-hydroxy-N-(tricyclo[3.3.1.1$^{3,7}$]dec-1-methyl)-benzamide prepared as described in step a) above (0.09 g) in acetonitrile (5 ml) was added caesium carbonate (0.257 g) and the reaction mixture was stirred for 10 minutes. 2-Dimethylaminoethyl chloride hydrochloride (0.055 g) was added and the resulting suspension was heated at reflux for 1.5 hours. The reaction mixture was then cooled to room temperature, diluted with diethyl ether and extracted with water. Drying over sodium sulphate ($Na_2SO_4$) followed by concentration under reduced pressure gave a residue which was subsequently purified by silica gel chromatography, eluting with 4% methanol in dichloromethane. Fractions containing product were concentrated under reduced pressure and the residue obtained was dissolved in diethyl ether. Hydrogen chloride (1 ml of a 1M solution in diethyl ether) was added dropwise and the resulting solid was triturated under diethyl ether and then dried in vacuo to leave the title compound as a white solid (0.098 g).

Melting point: 181–183° C.

MS (APCI+ve) 357 (M+H)$^{30}$ for free base $^1$H NMR (DMSO-d$_6$) δ 10.63 (1H, s), 8.18 (1H, t), 7.51 (1H, dd), 7.46 (1H, dt), 7.19 (1H, d), 7.08 (1H, t), 4.47 (2H, t), 3.48 (2H, d), 2.97 (2H, d), 2.84 (6H, s), 1.95 (3H, s), 1.67 (3H, d), 1.61 (3H, d), 1.41 (6H, d)

EXAMPLE 25

2-[[(Tricyclo[3.3.1.1$^{3,7}$]dec-1-ylmethyl)amino]carbonyl]phenyl-1-oxyacetic acid, 1,1-dimethylethyl ester

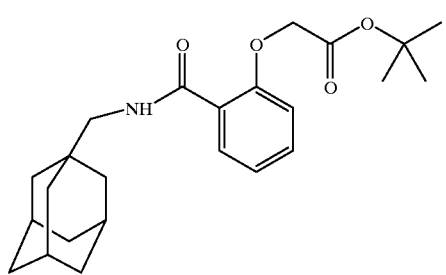

Prepared according to the method of Example 24 b) from 2-hydroxy-N-(tricyclo[3.3.1.1$^{3,7}$]dec-1-methyl)-benzamide (0.10 g) and tert-butyl bromoacetate (0.0.85 g) to give the title compound as a white solid (0.11 g).

Melting point: 101–103° C.

MS (APCI+ve) 400 (M+H)$^+$ $^1$H NMR (DMSO-d$_6$) δ 8.33 (1H, t), 7.86 (1H, dd), 7.45 (1H, dd), 7.13 (1H d), 7.08 (1H, dt), 4.88 (2H, s), 3.06 (2H, d), 1.92 (3H, s), 1.65 (3H, d), 1.60 (3H, d), 1.51 (6H, d), 1.44 (9H, s)

EXAMPLE 26

2-[[(Tricyclo[3.3.1.1$^{3,7}$]dec-1-ylmethyl)amino]carbonyl]phenyl-1-oxyacetic acid

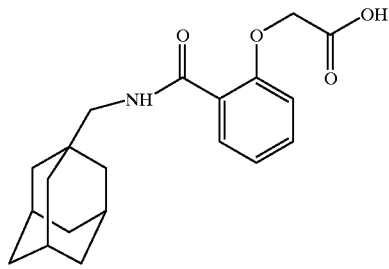

To a solution of the ester prepared as described in Example 25 above (0.085 g) in dichloromethane (0.75 ml) was added trifluoroacetic acid (1.5 ml). The reaction mixture was stirred at room temperature for three days and then concentrated under reduced pressure to leave a residue. The residue was thereafter co-evaporated with toluene and the beige solid obtained was triturated under diethyl ether to yield the title compound as a white solid (0.04 g).

Melting point: 186–187° C.

MS (APCI+ve) 342 (M+H)$^{30}$ $^1$H NMR (DMSO-d$_6$) δ 8.52 (1H, t), 7.88 (1H, dd), 7.46 (1H, dd), 7.14 (1H d), 7.08 (1H, dt), 4.89 (2H, s), 3.05 (2H, d), 1.93 (3H, s), 1.65 (3H, d), 1.59 (3H, d), 1.51 (6H, d)

EXAMPLE 27

2-(Methylsulphoxide)-N-(txicyclo[3.3.1.1$^{3,7}$]dec-1-methyl)-3-pyridine carboxamide

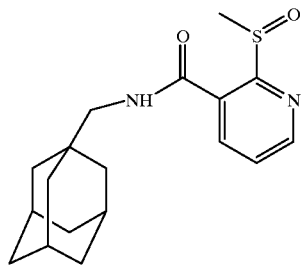

To an ice-cooled solution of the amide prepared as described in Example 19 above (1.00 g) in 80% aqueous methanol (20 ml) was added potassium peroxymonosulphate (4.00 g) portion wise. After stirring for 2 hours, the reaction mixture was poured onto saturated sodium metabisulphite solution and extracted with ethyl acetate. Combined organic extracts were washed with sodium metabisulphite solution and then brine, dried over magnesium sulphate (MgSO$_4$) and finally concentrated under reduced pressure to yield the title compound as a white solid (1.00 g).

Melting point: 214° C.

MS (APCI+ve) 333 (M+H)$^{30}$ $^1$H NMR (DMSO-d$_6$) δ 8.84 (1H, dd), 8.68 (1H, t), 8.06 (1H, dd), 7.65 (1H, dd), 2.95 (1H, m), 2.78 (3H, s), 1.94 (3H, s), 1.66 (3H, d), 1.62 (3H, d), 1.51 (6H, d)

EXAMPLE 28

N-(tricyclo[3.3.1.1$^{3,7}$]dec-1-methyl)-5-indole carboxamide

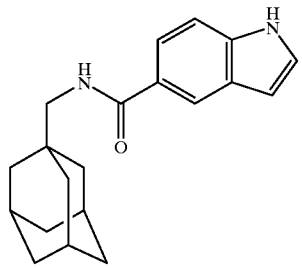

Prepared according to the method of Example 14 from 1-adamantanemethylamine (0.10 ml) and indole-5-carboxylic acid (0.09 g) to give the title compound as a white solid (0.09 g).

Melting point: 206–207° C.

MS (APCI+ve) 309 (M+H)$^+$ $^1$H NMR (DMSO-d$_6$) δ 11.28 (1H, s), 8.13 (1H, d), 8.09 (1H, t), 7.62 (1H, dd), 7.42 (1H, t), 7.40 (1H, d), 6.52 (1H, m), 3.00 (2H, d), 1.93 (3H, s), 1.65 (3H, d), 1.60 (3H, d), 1.51 (6H, d)

EXAMPLE 29

2-Amino-6-chloro-N-(2-[tricyclo[3.3.1.1$^{3,7}$]dec-1-yl]ethyl)-benzamide

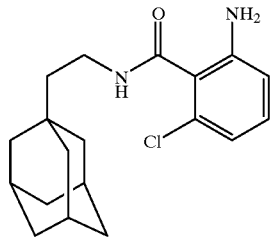

Prepared according to the method of Example 14 from 1-adamantaneethylamine hydrochloride (CN 26482-53-1) (0.105 g) and 2-amino-6-chlorobenzoic acid (0.132 g) and purified by supercritical fluid chromatography eluting with $CO_2$ in ethanol to give the title compound, contaminated with 0.35 mol equivalents of imidazole, as a white solid (0.046 g).

Melting point: 132–134° C.

MS (APCI+ve) 333/335 (M+H)[30]

$^1$H NMR (DMSO-d$_6$) δ 8.26 (1H, t), 7.01 (1H, t), 6.72 (1H, dd), 6.67 (1H, dd), 5.14 (2H, s), 3.23 (2H, m), 1.93 (3H, s), 1.70-1.59 (6H, m), 1.51 (6H, d), 1.31 (2H, m).

EXAMPLE 30

2-(2-Methylsulphonyl)-N-(tricyclo[3.3.1.1$^{3,7}$]dec-1-ylmethyl)-3-pyridine carboxamide

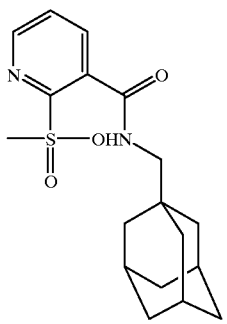

To an ice-cooled solution of the amide prepared as described in Example 19 (1.00 g) in 80% aqueous methanol (20 ml) was added potassium peroxymonosulphate (6.00 g) portion wise. After stirring for 24 hours, the reaction mixture was poured onto saturated sodium metabisulphite solution and extracted with ethyl acetate. Combined organic extracts were washed with sodium metabisulphite solution and then brine, dried over magnesium sulphate (MgSO$_4$) and finally concentrated under reduced pressure to yield the title compound as a white solid (1.00 g).

Melting point: 190° C.

MS (APCI+ve) 349 (M+H)[30]

$^1$H NMR (DMSO-d$_6$) δ 8.84 (1H, dd), 8.57(1H, t), 8.06 (1H, dd), 7.65 (1H, dd), 2.95 (2H, m), 2.78 (3H, s), 1.94 (3H, s), 1.66 (3H, d), 1.62 (3H, d), 1.51 (6H, d)

EXAMPLE 31

2-(2-Aminoethylthio)-N-(txicyclo[3.3.1.1$^{3,7}$]dec-1-ylmethyl)-3-pyridine carboxamide, trifluoroacetate

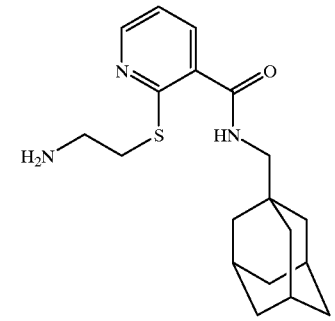

To a solution of the sulphone from Example 30 (0.1 g) in acetonitrile (3 ml) was added triethylamine (0.04 ml) and tert-butyl-N-(2-mercaptoethyl)carbamate (0.054 g). The reaction mixture was stirred and heated at reflux for 24 hours. The reaction mixture was cooled and the resulting solid collected by filtration. The solid was dissolved in dichloromethane (5 ml) and the solution treated with trifluoroacetic acid (1.0 ml). After stirring for 2 hours at ambient temperature, the reaction mixture was evaporated under reduced pressure, the residue was triturated with iso-hexane to give the title compound as a white solid (0.023 g).

Melting point: 184° C.

MS (APCI+ve) 346 (M+H)[30] for free base $^1$H NMR (DMSO-d$_6$) δ 8.52 (1H, dd), 8.39 (1H, t), 7.89 (2 H, bs), 7.83 (1H, dd), 7.25 (1H, dd), 3.30 (2H, t), 3.09 (2H, t), 2.94 (2H, d), 1.94 (3H, s), 1.66 (3H, d), 1.62 (3H, d), 1.51 (6H, d)

EXAMPLE 32

2-(2-(N,N-Dimethylamino)ethylamino)-N-(tricyclo[3.3.1.1$^{3,7}$]dec-1-ylmethyl)-3-pyridine carboxamide, dihydrochloride

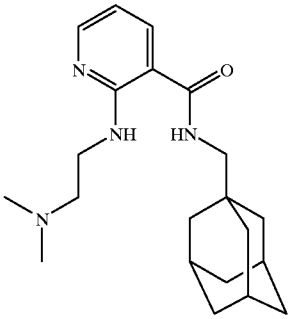

To a solution of the sulphone from Example 30 (0.1 g) in acetonitrile (3 ml) was added triethylamine (0.04 ml) and N,N-dimethylethylenediamine (0.030 g). The reaction mixture was stirred and heated at 80° C. in a sealed tube for 48 hours. The reaction mixture was cooled, diluted with ethyl acetate, washed with brine and dried over MgSO$_4$. A solution of hydrogen chloride in diethyl ether (1.0 ml of 1.0M) was added and the solvents evaporated under reduced pressure. The residue was recrystallised from acetonitrile to give the title compound as a white solid. (0.025 g).

Melting point: 258–260° C.

MS (APCI+ve) 357 (M+H)[30] for free base $^1$H NMR (DMSO-d$_6$) δ 10.1 (1H, bs), 8.60 (1H, bs), 8.20 (1H, bd), 8.15 (1H, dd), 6.84 (1H, t), 3.90 (2H, bm), 3.30 (2H,bm), 2.95 (2H, d), 1.94 (3H, s), 1.66 (3H, d), 1.62 (3H, d), 1.51 (6H, d)

EXAMPLE 33

2-(2-(Pyrrolidin-1-yl)ethylamino)-N-(tricyclo[3.3.1.1$^{3,7}$]dec-1-ylmethyl)-3-pyridine carboxamide, dihydrochloride

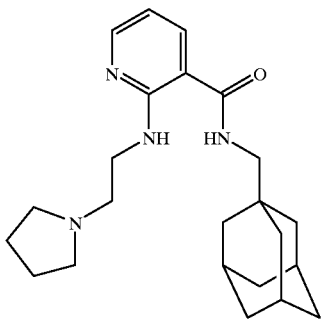

To a solution of the sulphone from Example 30 (0.1 g) in dimethylformamide (3 ml) was added triethylamine (0.04 ml) and N-(2-aminoethyl)pyrrolidine (0.050 g). The reaction mixture was stirred and heated at 80° C. in a sealed tube for 24 hours before being cooled to room temperature and diluted with ethyl acetate, washed with brine and dried over MgSO$_4$. The solvent was evaporated under reduced pressure and the residue purified by silica gel chromatography eluting with 1–3% methanol in dichloromethane. The fractions containing product were combined, treated with a solution of hydrogen chloride in diethyl ether (1.0 ml of 1.0M) and the solvent evaporated under reduced pressure to give the title compound as a white solid (0.010 g).

Melting point: 266–268° C.

MS (APCI+ve) 383 (M+H)[30] for free base $^1$H NMR (DMSO-d$_6$) δ 8.60 (1H, bs), 8.20 (2H, m), 6.80 (1H, t), 3.90 (2H, bm), 3.40 (6H, m), 2.95 (2H, d), 1.94 (7H, m), 1.66 (3H, d), 1.62 (3H, d), 1.51 (6H, d)

EXAMPLE 34

2-(Methylamino)-N-(tricyclo[3.3.1.1$^{3,7}$]dec-1-ylmethyl)-3-pyridine carboxamide, dihydrochloride

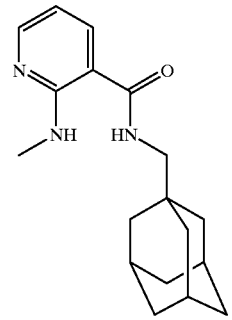

Prepared according to the method of Example 33 using the sulphone from Example 30 (0.1 g) and methylamine (0.2 ml of a 2.0M solution in tetrahydrofuran) to give the title compound as a white solid (0.010 g).

Melting point: 160–162° C.

MS (APCI+ve) 300 (M+H)[30] for free base $^1$H NMR (DMSO-d$_6$) δ 8.80 (1H, t), 8.40 (1H, d), 8.10 (1H, dd), 6.90 (1H, t), 3.05 (3H, s), 2.98 (2H, d), 1.94 (3H, s), 1.66 (3H, d), 1.62 (3H, d), 1.51 (6H, d)

EXAMPLE 35

2-(Dimethylanino)-N-(tricyclo[3.3.1.1$^{3,7}$]dec-1-ylmethyl)-3-pyridine carboxamide, hydrochloride

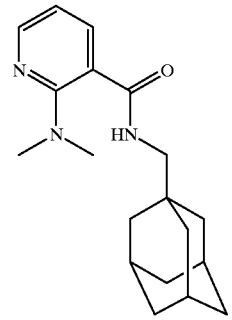

Prepared according to the method of Example 33 using the sulphone from Example 30 (0.1 g) and dimethylamine (0.2 ml of a 2.0M solution in tetrahydrofuran) to give the title compound as a white solid (0.025 g).

Melting point: 204–205° C.

MS (APCI+ve) 314 (M+H)[30] for free base $^1$H NMR (DMSO-d$_6$) δ 8.56 (1H, t), 8.10 (1H, dd), 7.90 (1H, d), 6.95 (1H, t), 3.05 (6H, s), 2.98 (2H, d), 1.94 (3H, s), 1.66 (3H, d), 1.62 (3H, d), 1.51 (6H, d)

EXAMPLE 36

2-(Pyrrolidin-1-yl) N-(tricyclo[3.3.1.1^{3,7}]dec-1-ylmethyl)-3-pyridine carboxamide, dihydrochloride

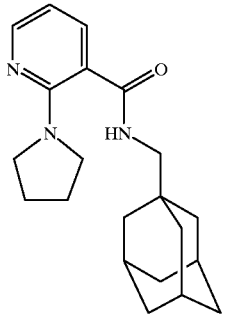

Prepared according to the method of Example 33 using the sulphone from Example 30 (0.1 g) and pyrrolidine (0.1 ml) to give the title compound as a white solid (0.009 g).

Melting point: 157–158° C.

MS (APCI+ve) 340 (M+H)[30] for free base $^1$H NMR (DMSO-d$_6$) δ 8.56 (1H, t), 8.05 (1H, dd), 7.88 (1H, d), 6.90 (1H, t), 3.65 (4H, bs), 2.98 (2H, d), 1.98 (7H, bs), 1.66 (3H, d), 1.62 (3H, d), 1.51 (6H, d)

EXAMPLE 37

2-(2,5-Dimethoxyphenylthio)-N-(tricyclo[3.3.1.1^{3,7}]dec-1-ylmethyl)-3-pyridine carboxamide

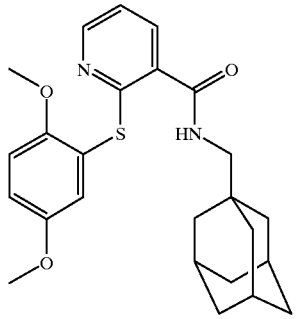

Prepared according to the method of Example 14 from 1-adamantanemethylamine (0.77 g) and 2-(2,5-dimthoxyphenylthio)pyridine-3-carboxylic acid (1.36 g) to give the title compound as a white solid (1.20 g).

Melting point: 135–136° C.

MS (APCI+ve) 440 (M+H)[30]

$^1$H NMR DMSO-d$_6$ ) δ 8.45 (1H , t), 8 .30 (1H, dd), 7.80 (1H, dd), 7.20 (1H, dd), 6.95 (3H, m), 3.69 (3H, s), 3.62 (3H, s), 2.98 (2H, d), 1.98 (3H, s), 1.66 (3H, d), 1.62 (3H, d), 1.51 (6H, d)

EXAMPLE 38

2-Chloro-5-methylthio-N-(tricyclo[3.3.1.1^{3,7}]dec-1-ylmethyl)-benzamide

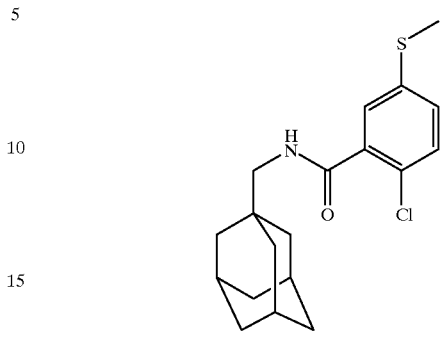

To a solution of 2-chloro-5-methylthiobenzoic acid (0.2 g) and 1-hydroxy benzotriazole (0.13 g) in dichloromethane (10 ml) was added 1-adamantanemethylamine (0.17 ml). The mixture was stirred 5 min and then 1,3-dicyclohexylcarbodiimide (0.2 g) was added. Stirring was continued overnight. The resulting precipitate was filtered and the filtrate concentrated under reduced pressure. The residue was partitioned between dichloromethane and water and the organic layer was separated, washed with dilute hydrochloric acid, aqueous sodium bicarbonate and brine and then dried over magnesium sulphate (MgSO$_4$). The organic layer was concentrated under reduced pressure and the residue purified by silica gel chromatography (eluting with 20% ethyl acetate in isohexanes) to yield the title compound as a white solid (0.31 g).

Melting point: 126–127° C.

MS (APCI+ve) 350 (M+H)[30]

$^1$H NMR (CDCl$_3$) δ 7.55 (1H, s), 7.30 (1H, d), 7.22 (1H, dd), 6.25 (2H, bs), 3.18 (2H,d), 2.49 (3H, s), 2.01 (3H, bs), 1.74 (3H, d), 1.65 (3H, d), 1.58 (6H, d)

EXAMPLE 39

2-(2-(N,N-Dimethylamino)ethylthio)-N-(tricyclo[3.3.1.1^{3,7}]dec-1-ylmethyl)-benzamide

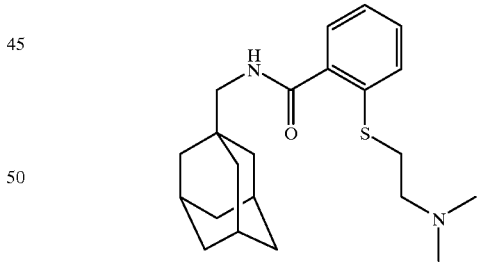

a) 2,2'-Dithiobis[N-(tricyclo[3.3.1.1^{3,7}]dec-1-ylmethyl)-benzamide]

Prepared according to the method of Example 14 from 1-adamantanemethylamine (0.23 g), 4-dimethylaminopyridine (0.006 g) and 2,2'dithiosalicylic acid (0.2 g) to give the sub-title compound as an off-white solid (0.12 g).

b) 2-(2-(N,N-Dimethylamino)ethylthio)-N-(tricyclo[3.3.1.1^{3,7}]dec-1-ylmethyl)-benzamide Sodium borohydride (0.037 g) was added batchwise to a stirred solution of the product from step a) (0.12 g) in ethanol (4.6 ml) under nitrogen. The reaction mixture was stirred for 0.5 h., the solvent evaporated under reduced pressure and the residue diluted with water. The aqueous solution was acidified to pH 6 with acetic acid and the product extracted with dichloromethane. The organic extract was washed with water and dried over magnesium sulphate (MgSO$_4$). Concentration of the organic phase under reduced pressure yielded an oil (0.11 g).

To a solution of the oil in dimethylformamide (5 ml) was added 2-dimethylamino ethyl chloride hydrochloride (0.063 g) and caesium carbonate (0.3 g). The resulting suspension was stirred at room temperature overnight. The reaction mixture was diluted with ethyl acetate and washed with water. Organic extracts were dried over magnesium sulphate (MgSO$_4$) and concentrated under reduced pressure to give a gum which was purified by silica gel chromatography (eluting with ethyl acetate and 0.1 to 1% ammonium hydroxide) to yield a gum. Hydrogen chloride (2 ml of a 1M solution in diethyl ether) was added dropwise to a solution of the gum in dichloromethane. The solvents were removed under reduced pressure and the residue was triturated under ethyl acetate and ether to leave the title compound as a white solid (0.03 g).

Melting point: 193–195° C.

MS (APCI+ve) 373/374 (M+H)$^{30}$ for free base $^1$H NMR (CDCl$_3$) δ 7.62 (1H,d), 7.42 (3H,m), 6.13 (1H,bs), 3.39 (2H,m), 3.17 (4H,m), 2.78 (6H,s), 2.02 (3H, bs), 1.68 (12H,m).

EXAMPLE 40

2-(4-Methoxyphenylthio)-N-(tricyclo[3.3.1.1$^{3,7}$]dec-1-ylmethyl)-3-pyridine carboxamide

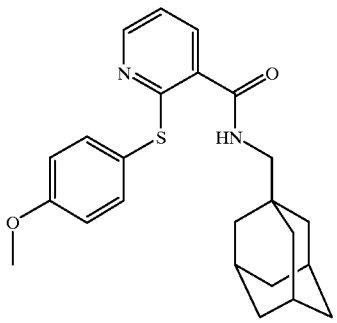

To a solution of the sulphone from Example 30 (1.0 g) in acetonitrile (30 ml) was added triethylamine (0.40 ml) and 4-methoxythiophenol (0.402 g). The reaction mixture was stirred and heated at reflux for 24 hours before being concentrated under reduced pressure. The residue was purified by silica gel chromatography, eluting with diethyl ether. Fractions containing the product were combined and evaporated under reduced pressure to leave the title compound as a white solid (0.50 g).

Melting point: 130–131° C.

MS (APCI+ve) 410 (M+H)$^+$ $^1$H NMR (DMSO-d$_6$) δ 8.45 (1H, t), 8.31 (1H, dd), 7.76 (1H, dd), 7.40 (2 H, m), 7.20 (1H, dd), 7.0 (2H, m), 3.30 (2H, t), 3.09 (2H, t), 2.94 (2H, d), 1.94 (3H, s), 1.66 (3H, d), 1.62 (3H, d), 1.51 (6H, d)

EXAMPLE 41

2-Chloro-3-fluoro-N-(tricyclo[3.3.1.1$^{3,7}$]dec-1-ylmethyl)-benzamide

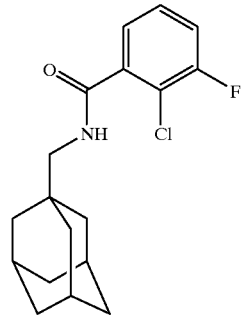

A solution of 2-chloro-3-fluorobenzoic acid (0.098 g) and carbonyldiimidazole (0.091 g), in N,N-dimethylformamide (3.0 ml) was stirred for 2.5 hours at room temperature. 1-Adamantanemethylamine (0.1 ml) was then added and stirring continued overnight. The reaction mixture was partitioned between ethyl acetate and 2N hydrochloric acid and the organic layer was separated, washed with 10% aqueous sodium hydroxide, water and brine and then dried over sodium sulphate (Na$_2$SO$_4$). The organic layer was subsequently concentrated under reduced pressure to yield the title compound as a white solid (0.138 g).

Melting point: 149–151° C.

MS (APCI+ve) 322/324 (M+H)$^+$ $^1$H NMR (DMSO-d$_6$) δ 8.42 (1H, t), 7.50 - 7.40 (2H, m), 7.29 - 7.24 (1H, m), 2.94 (2H, d), 1.94 (3H, s), 1.64 (6H, dd), 1.53 (6H, m)

EXAMPLE 42

2-Bromo-5-fluoro-N-(tricyclo[3.3.1.1$^{3,7}$]dec-1-ylmethyl)-benzamide

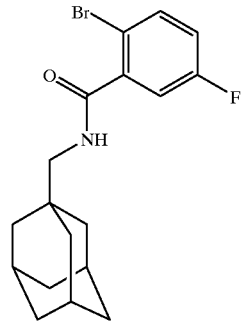

Prepared according to the method of Example 41 from 1-adamantanemethylamine (0.1 ml) and 2-bromo-5-fluorobenzoic acid (0.123 g) to give the title compound as a white solid (0.140 g).

Melting point: 143–144° C.

MS (APCI+ve) 322/324 (M+H)$^+$ $^1$H NMR (DMSO-d$_6$) δ 8.40 (1H, t), 7.56 - 7.52 (1H, dd), 7.34 -7.27 (2H, m), 2.93 (2H, d), 1.94 (3H, s), 1.63 (6H, dd), 1.52 (6H, m)

EXAMPLE 43

2-Chloro-5-fluoro-N-(tricyclo[3.3.1.1$^{3,7}$]dec-1-ylmethyl)-benzamide

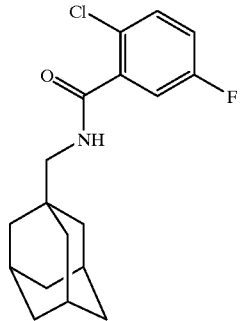

Prepared according to the method of Example 41 from 1-adamantanemethylamine (0.1 ml) and 2-chloro-5-fluorobenzoic acid (0.098 g) to give the title compound as a white solid (0.165 g).

Melting point: 176–177° C.

MS (APCI+ve) 366/367 (M+H)[30]

$^1$H NMR (DMSO-d$_6$) δ 8.37 (1H, t), 7.71 - 7.65 (1H, dd), 7.28 -7.20 (2H, m), 2.92 (2H, d), 1.94 (3H, s), 1.64 (6H, dd), 1.53 (6H, d)

EXAMPLE 44

2-(2,5-Dihydroxyphenylthio)-N-(tricylo[3.3.1.1$^{3,7}$]dec-1-ylmethyl)-3-pyridine carboxamide

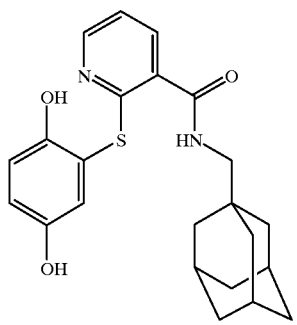

To a solution of the dimethoxy compound from Example 37 (1.0 g) in dichloromethane (20 ml) at −78° C., was added boron tribromide (5.5 ml of a 1M solution in dichloromethane. The reaction mixture was stirred for 24 hours, warming to ambient temperature. Methanol (5 ml) was added and the solvent was removed under reduced pressure and the residue purified by silica gel chromatography eluting with dichloromethane, ethyl acetate, acetic acid (4:1:0.1). The fractions containing product were combined and the solvent removed under reduced pressure to give the title compound as a white solid (0.40 g).

Melting point: 108–110° C.

MS (APCI+ve) 411 (M+H)$^+$ $^1$H NMR (DMSO-d$_6$) δ 8.95 (1H, s), 8.83 (1H, s), 8.44 (1H, t), 8.32 (1 H, d), 7.75 (1H, dd), 7.20 (1H, dd), 6.75 (3H, m), 2.94 (2H, d), 1.94 (3H, s), 1.66 (3H, d), 1.62 (3H, d), 1.51 (6H, d)

EXAMPLE 45

3-[[(Tricyclo[3.3.1.1$^{3,7}$]dec-1-ylmethyl)amino]carbonyl]pyridyl-2-thioacetic acid

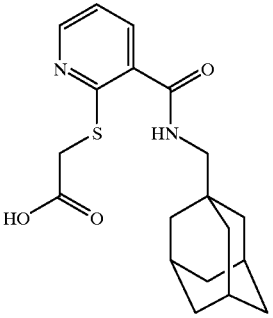

To a solution of the sulphone from Example 30 (0.1 g) in acetonitrile (3 ml) was added triethylamine (0.04 ml) and methyl thioglycate (0.050 g). The reaction mixture was stirred and heated at reflux for 24 hours before cooling to room temperature and the solvent evaporated under reduced pressure. The residue was dissolved in ethanol (2 ml) and treated with 2M sodium hydroxide. The reaction mixture was stirred at ambient temperature for 24 hours, acidified with 2M hydrochloric acid and extracted into ethyl acetate. The extracts were dried (MgSO$_4$) and evaporated under reduced pressure. The product was purified by silica gel chromatography eluting with 0–3% methanol in dichloromethane. Fractions containing product were combined and evaporated under reduced pressure to give the title compound as a white solid (0.008 g).

Melting point: 147–150° C.

MS (APCI+ve) 361 (M+H)[30]

$^1$H NMR (DMSO-d$_6$) δ 8.53(1H, t), 8.45 (1H, dd), 7.89 (2 H, bs), 7.20 (1H, dd), 3.80 (2H, s), 2.94 (2H, d), 1.94 (3H, s), 1.66 (3H, d), 1.62 (3H, d), 1.51 (6H, d)

EXAMPLE 46

(2-Chloro-6-methyl)-N-(tricylo[3.3.1.1$^{3,7}$]dec-1-ylmethyl)-3-pyridine carboxamide

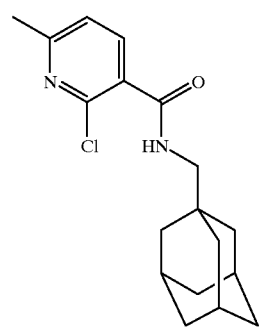

Prepared according to the method of Example 14 from 1-adamantanemethylamine (0.20 g) and 2-chloro-6-methyl-3-pyridine carboxylic acid (0.208 g) to give the title compound as a white solid (0.24 g).

Melting point: 192–193° C.

MS (APCI+ve) 320/322 (M+H)[30]

$^1$H NMR (DMSO-$d_6$) δ 8.39 (1H, t), 7.75 (1H, d), 7.31 (1H, d), 2.96 (2H, d), 2.45 (3H, s), 1.95 (3H, s), 1.67 (3H, d), 1.61 (3H, d), 1.53 (6H, d)

EXAMPLE 47

3-[[(Tricyclo[3.3.1.1$^{3,7}$]dec-1-ylmethyl)amino]carbonyl]pyridyl-2-(4-phenylthio) oxyacetic acid

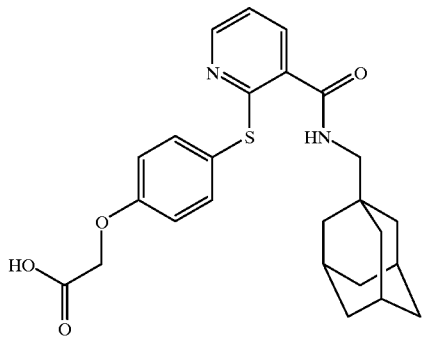

To a solution of the methoxy compound from Example 40 (0.56 g) in dichloromethane (10 ml) at −78° C., was added boron tribromide (1.5 ml of a 1M solution in dichloromethane). The reaction mixture was stirred for 24 hours, warming to ambient temperature. Methanol (5 ml) was added, the reaction mixture poured onto saturated sodium chloride solution and extracted into ethyl acetate. The organic layer was dried over MgSO$_4$ and the solvent was removed under reduced pressure to leave a white solid which was dissolved in dimethylformamide (10 ml), treated with ethylbromoacetate (0.1 ml) and potassium carbonate (0.050 g). The mixture was stirred at ambient temperature for 24 hours, diluted with saturated sodium chloride solution and extracted with ethyl acetate. The organic phase was further washed with saturated sodium chloride solution, dried over MgSO$_4$ and the solvent was removed under reduced pressure to leave a white solid. The residue was dissolved in dioxane (10 ml), treated with 2M sodium hydroxide (5 ml) solution and stirred at ambient temperature for 24 hours, acidified with 2M hydrochloric acid and filtered to give a white solid which was purified by silica gel chromatography eluting with 25% methanol in dichloromethane. Fractions containing product were combined and the solvent removed under reduced pressure to leave the title compound as a white solid (0.045 g).

Melting point: 185–186° C.

MS (APCI+ve) 453 (M+H)[30]

$^1$H NMR (DMSO-$d_6$) δ 8.47(1H, t), 8.25 (1H, dd), 7.75 (1H, dd), 7.35 (2H, d), 7.18 (1h, m), 6.80 (2H, d), 4.15 (2H, s), 3.0 (2H, d), 2.0 (3H, s), 1.67 (3H, d), 1.61 (3H, d), 1.53 (6H, d)

EXAMPLE 48

2-(4-(3-N,N-dimethylamino)propyloxyphenylthio)-N-(tricyclo[3.3.1.1$^{3,7}$]dec-1-ylmethyl)-3-pyridine carboxamide, dihydrochloride

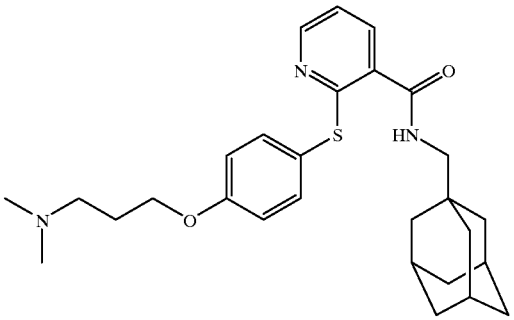

To a solution of the methoxy compound from Example 40 (0.56 g) in dichloromethane (10 ml) at −78° C., was added boron tribromide (1.5 ml of a 1M solution in dichloromethane). The reaction mixture was stirred for 24 hours, warming to ambient temperature. Methanol (5 ml) was added, the reaction mixture poured onto saturated sodium chloride solution and extracted into ethyl acetate. The organic layer was dried over MgSO$_4$ and concentrated under reduced pressure to leave a white solid. A portion of this solid (0.10 g) was dissolved in dimethylformarnide (5 ml), treated with potassium carbonate (0.072 g) and N,N-dimethyl-3-chloropropylamine hydrochloride (0.045 g) and stirred at ambient temperature for 24 hours. The reaction mixture was diluted with saturated sodium chloride solution and extracted with ethyl acetate. The organic phase was further washed with saturated sodium chloride solution, dried over MgSO$_4$, and a solution of hydrogen chloride in diethylether (4 ml of 2.0M) added. The solvent was removed under reduced pressure to leave a gum which was recrystallised from acetonitrile to give the title compound as a white solid (0.018 g).

Melting point: 177–178° C.

MS (APCI+ve) 480 (M+H)[30]

$^1$H NMR (DMSO-$d_6$) δ 10.43 (1H, bs), 8.46 (1H, t), 8.30 (1H, dd), 7.78 (1H, dd), 7.4 (2H, d), 7.2 (1H, dd), 7.0 (2H, d), 4.09 (2H, t), 3.20 (2H, m), 3.0 (2H, d), 2.8 (6H. 2s), 2.2 (2H, m), 1.95 (3H, s), 1.6 (12H. m).

EXAMPLE 49

(2-Methylthio-6-methyl)-N-(tricyclo[3.3.1.1^{3,7}]dec-1-ylmethyl)-3-pyridine carboxamide

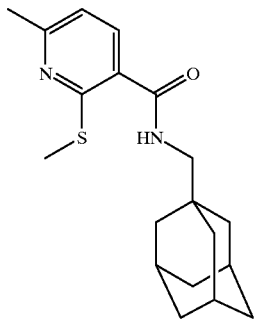

To a solution of the chloro-pyridine from Example 46 (0.10 g) in acetonitrile (3 ml) was added sodium methanethiolate (0.1 g). The reaction mixture was stirred and heated at 80° C. in a sealed tube for 24 hours. The reaction mixture was cooled, diluted with ethyl acetate, washed with saturated sodium chloride solution and dried over MgSO$_4$. The solvent was evaporated under reduced pressure and the residue triturated with diethyl ether to give the title compound as a pale yellow solid (0.028 g).

Melting point: 160–161° C.

MS (APCI+ve) 331 (M+H)[30]

$^1$H NMR (DMSO-d$_6$) δ 8.22 (1H, t), 7.64 (1H, d), 7.02 (1H, d), 2.91 (2H, d), 2.51 (3H, s), 2.40 (3H, s), 1.93 (3H, s), 1.65 (3H, d), 1.60 (3H, d), 1.53 (6H, d)

EXAMPLE 50

2-[[(Tricyclo[3.3.1.1^{3,7}]dec-1-ylmethyl)amino]carbonyl]phenyl-1-oxybutyric acid

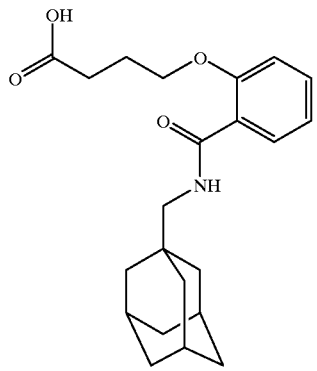

a) 2-[[(Tricyclo[3.3.1.1^{3,7}]dec-1-ylmethyl)amino]carbonyl]phenyl-1-oxybutyric acid, methyl ester A suspension of 2-hydroxy-N-(tricyclo[3.3.1.1^{3,7}]dec-1-ylmethyl)benzamide, from Example 24 step a) (0.061 g), and caesium carbonate (0.069 g) in acetonitrile (3 ml) was heated at 40° C. until homogeneous. Methyl 4-bromobutyrate (0.032 ml) was added and the resulting mixture was heated at reflux temperature for 0.5 hours. The reaction mixture was cooled to room temperature, poured into water and extracted with ethyl acetate (x 3). The combined organic extracts were washed with water and saturated aqueous sodium chloride solution and dried over sodium sulphate (Na$_2$SO$_4$) followed by concentration under reduced pressure to give the sub-title compound as a colourless oil.

MS (APCI+ve) 386 (M+H)[30]

b) 2-[[(Tricyclo[3.3.1.1^{3,7}]dec-1-ylmethyl)amino]carbonyl]phenyl-1-oxybutyric acid A suspension of 2-[[(tricyclo[3.3.1.1^{3,7}]dec-1-ylmethyl)amino]carbonyl]phenyl-1-oxybutyric acid methyl ester, from step a) and lithium hydroxide monohydrate (0.027 g) in 3:1 methanol/water was stirred at room temperature overnight. The resulting homogeneous solution was acidified with 2N hydrochloric acid and extracted with diethyl ether (x 3). The ethereal layers were combined and washed with saturated aqueous sodium chloride solution. Drying over sodium sulphate (Na$_2$SO$_4$) followed by concentration under reduced pressure yielded an opaque gum which gave the titled compound as a colourless solid upon trituration with diethyl ether and iso-hexane (0.030 g).

Melting point: 109–113° C.

MS (APCI+ve) 372 (M+H)[30]

$^1$H NMR (DMSO-d$_6$) δ 7.99 (1H, t), 7.74 (1H, d), 7.44 (1H, t), 7.13 (1H, d), 7.02 (1H, t), 4.13 (2H, t), 3.02 (2H, d), 2.42 (2H, t), 2.02 (2H, m), 1.94 (3H, s), 1.64 (6H, dd), 1.51 (6H, m), carboxylic acid proton not visible.

EXAMPLE 51

2-Chloro-5-hydroxy-N-(tricyclo[3.3.1.1^{3,7}]dec-1-ylmethyl)-benzamide

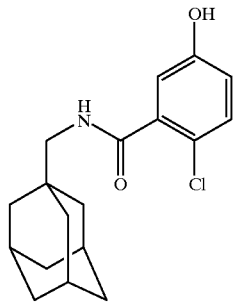

Prepared according to the method of Example 14 from 2-chloro-5-hydroxybenzoic acid (0.3 g) and 1-adamantanemethylamine (0.31 ml) to give the title compound as a white solid (0.15 g).

Melting point: 263–264° C.

MS (APCI+ve) 320 (M+H)[30]

$^1$H NMR (DMSO-d$_6$) δ 9.85(1H,s), 8.25 (1H, t), 7.24(1H, d), 6.76-6.82(2H, m), 2.90 (2H,d), 1.93(3H, s), 1.67 (3H, d), 1.57 (3H, d), 1.51 (6H, s)

EXAMPLE 52

2-Chloro-3-nitro-N-(tricyclo[3.3.1.1$^{3,7}$]dec-1-ylmethyl)-benzamide

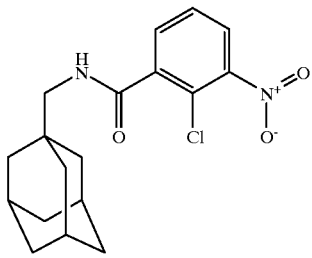

Prepared according to the method of Example 14 from 1-adamantanemethylamine (1.0 g) and 2-chloro-3-nitrobenzoic acid (1.22 g) to give the title compound as a yellow solid (1.7 g).

Melting point: 185° C.

MS (APCI+ve) 348/350 (M+H)$^{30}$ $^1$H NMR (CDCl$_3$) δ 7.83 (1H, d), 7.74 (1H, d), 7.48 (1H, t), 6.0(1H, bs), 3.18 (2H, d), 2.0 (3H, bs), 1.8 (12H, m)

EXAMPLE 53

2-Chloro-5-nitro-N-(tricylo[3.3.1.1$^{3,7}$]dec-1-ylmethyl)-benzamide

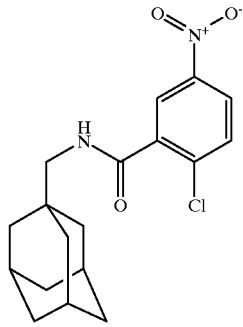

Prepared according to the method of Example 14 from 1-adamantanemethylamine (1.0 g) and 2-chloro-5-nitrobenzoic acid (1.22 g) to give the title compound as a yellow solid (1.7 g).

Melting point: 178° C.

MS (APCI+ve) 348/350 (M+H)$^{30}$ $^1$H NMR (CDCl$_3$) δ 8.53 (1H, d), 8.2 (1H, dd), 7.6 (1H, d), 6.2 (1H, bs), 3.2 (2H, d), 2.0 (3H,bs), 1.8 (12H, m)

EXAMPLE 54

3-Amino-2-chloro-N-(tricyclo[3.3.1.1$^{3,7}$]dec-1-ylmethyl)-benzamide

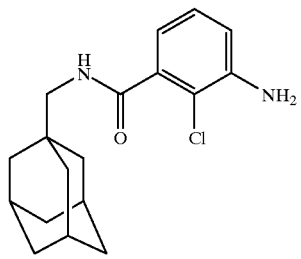

A solution of the nitro compound from Example 52 (0.50 g) and ammonium chloride (0.5 g) were dissolved in 50% aqueous ethanol. Iron powder (0.5 g) was added and the mixture stirred at reflux temperature for 3 hr before being cooled and solids removed by filtration. The filtrate was treated with 10% sodium hydroxide solution and the product extracted into ethyl acetate. The organic solution was washed with brine, dried over sodium sulphate (Na$_2$SO$_4$) and concentrated to give a residue which was purified by silica gel chromatography to give the title compound as a white powder (0.45 g).

Melting point: 154° C.

MS (APCI+ve) 319/21 (M+H)$^{30}$ $^1$H NMR (CDCl$_3$) 7.12 (1H, t), 6.91 (1H, dd), 6.79 (1H, dd), 5.92 (1H, bs), 4.19 (2H, bs), 3.15 ( 2H, d), 2.0 (3H,L s), 1.8 (12H, m)

EXAMPLE 55

5-Amino-2-chloro-N-(tricyclo[3.3.1.1$^{3,7}$]dec-1-ylmethyl)-benzamide

Prepared according to the method of Example 54 from the nitro compound from Example 53 (0.50 g) to give the title compound as a white solid (0.4 g).

Melting point: 214° C.

MS (APCI+ve) 319/21 (M+H)$^+$ $^1$H NMR (DMSO-d$_6$) δ 8.14 (1H, t), 7.03 (1H, dd), 6.56 (2H, m), 5.36 (2H, s), 2.89 (2H, d), 1.95 (3H, s), 1.7 (12H, m)

EXAMPLE 56

2-Chloro-3-(N,N-dimethylamino)ethylamino-N-(tricyclo[3.3.1.1$^{3,7}$]dec-1-ylmethyl)-benzamide

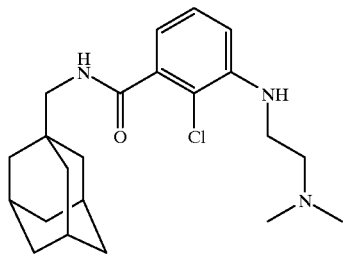

A mixture of the amino compound from Example 54 (0.10 g), potassium carbonate (0.087 g) and N-(2-chloroethyldimethylamine hydrochloride was stirred and heated at 138° C. for 72 hr. The residue was dissolved in water and the product extracted into ethyl acetate. The organic extract was washed with brine, dried over sodium sulphate ($Na_2SO_4$) and concentrated to give an oil which was purified by Supercritical Fluid Chromatography eluting with $CO_2$/methanol/0.1% diethylamine to give an oil. Addition of excess ethereal hydrogen chloride solution gave a solid which was triturated under an ether/ethanol/dichloromethane mixture to give a colourless powder (0.04 g).

Melting point: 221° C.

MS (APCI+ve) 390/392 (M+H)$^{30}$ $^1$H NMR (DMSO-$d_6$) δ 10.08 (1H, bs), 8.2 (1H, t), 7.2 (1H, t), 6.85 (1H, d), 6.62 (1H, d), 5.8 (1H, t), 3.6 (2H, m), 3.2 (2H, m), 2.9 (2H, d), 2.8 (6H, bs), 1.9 (3H, s), 1.7 (12H, m).

EXAMPLE 57

2-Chloro-5-(N,N-dimethylamino)ethylamino-N-(tricyclo[3.3.1.1$^{3,7}$]dec-1-ylmethyl)-benzamide

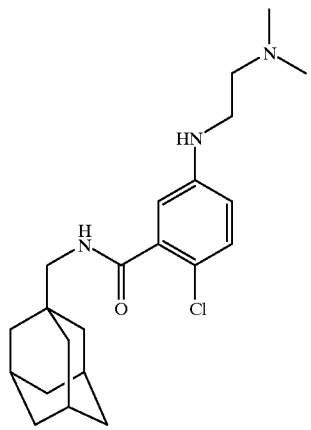

Prepared by the method of Example 56 from the amino compound of Example 55 (0.10 g) to give the title compound as a colourless solid (0.035 g).

Melting point: 215° C.

MS (APCI+ve) 390/92 (M+H)$^{30}$ $^1$H NMR (DMSO-$d_6$) δ 10.05 (1H, bs), 8.18 (1H, t), 7.18 (1H, d), 6.7 (1H, m), 6.66 (1H, m), 6.2 (1H, bs), 3.4 (2H, t), 3.2 (2H, t), 2.9 (2H, d), 2.8 (6H, bs), 1.9 (3H, s), 1.7 (12H, m).

EXAMPLE 58

2-Chloro-5-(N,N-dimethylamino)ethylthio-N-(tricyclo[3.3.1.1$^{3,7}$]dec-1-ylmethyl)-benzamide, fumarate

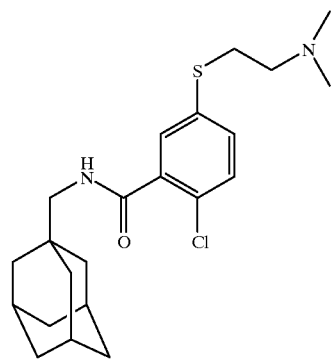

a) 2-Chloro-5-methylsulphinyl-N-(tricyclo[3.3.1.1$^{3,7}$]dec-1-ylmethyl)-benzamide A solution of amide from Example 38 (0.2 g) in chloroform (5 ml) was treated with 70% m chloroperbenzoic acid (0.14 g). The reaction mixture was stirred for two days, calcium hydroxide (0.09 g) added and after stirring for a further 0.5 h the mixture was filtered. The filtrate was concentrated under reduced pressure to yield the sub-title product as a white solid (0.23 g).

b) 2-Chloro-5-(N,N-dimethylamino)ethylthio-N-(tricyclo[3.3.1.1$^{3,7}$]dec-1-ylmethyl)-benzamide, fumarate.

To a solution of the sulphoxide from step a) (0.22 g) in dichloromethane (1 ml) was added trifluoroacetic anhydride (1.1 ml) and the reaction mixture was heated to reflux temperature for 2 h. The reaction mixture was cooled to room temperature and the solvent evaporated under reduced pressure. A solution of the residue in triethylamine/methanol (10 ml 1:1) was treated with 2-dimethylaminoethyl chloride hydrochloride (0.086 g) and the reaction mixture stirred at room temperature overnight. The solvent was removed under reduced pressure and the residue purified by silica gel chromatography (eluting with 10–20% methanol in ethyl acetate) to yield the product as a gum. Fumaric acid (0.0045 g) was added to a solution of the gum in dichloromethane (10 ml). The solvent was removed under reduced pressure to leave the title compound as a viscous gum (0.023 g).

MS (APCI+ve) 407/409 MH)$^{30}$ for free base $^1$H NMR (DMSO-$d_6$) δ 8.35 (1H, m), 7.39 (2H, m), 7.28(1H, d), 6.60 (1.5H,s), 3.13 (2H,t), 2.93 (2H,d), 2.57 (2H,t), 2.23 (6H,s), 1.95 (3H,bs), 1.63 (6H,q), 1.52 (6H,d).

EXAMPLE 59

2-Chloro-3-hydroxy-N-(tricyclo[3.3.1.1$^{3,7}$]dec-1-ylmethyl)-benzamide

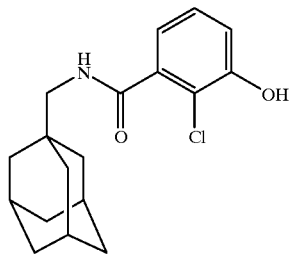

Prepared according to the method of Example 38 using 2chloro-3-hydroxybenzoic acid (0.39 g), 1-hydroxy benzotriazole (0.31 g), 1-adamantanemethylamine (0.4 ml) and 1,3-dicyclo-hexylcarbodiimide (0.47 g) to yield the title compound as a white solid (0.29 g).

Melting point: 234–235° C.
MS (APCI+ve) 320 (M+H)[30]
$^1$H NMR (DMSO-d$_6$) δ 8.20 (1H, t), 7.15 (1H, m), 6.95 (1H, d), 6.89 (1H, d), 2.91 (2H, d), 1.95 (3H, bs), 1.64 (6H, q), 1.52 (6H, d)

EXAMPLE 60

2-Chloro5-(N,N-dimethylamino)ethyloxy-N-(tricyclo[3.3.1.1$^{3,7}$]dec-1-ylmethyl)-benzamide

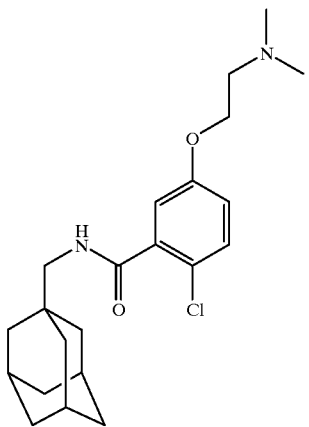

To a solution of 2-chloro-5-hydroxy-N-(tricyclo[3.3.1.1$^{3,7}$]dec-1-ylmethyl)benzamide from Example 51 (0.05 g) in acetonitrile (5 ml) was added potassium carbonate (0.065 g) and 2-dimethylaminoethyl chloride hydrochloride (0.037 g). The reaction mixture was stirred and heated at reflux temperature for 48 hours. The reaction mixture was evaporated under reduced pressure and residue dissolved in ethyl acetate and washed with brine. Drying over sodium sulphate (Na$_2$SO$_4$), followed by concentration under reduced pressure gave a residue which was subsequently purified by supercritical chromatography, eluting with CO$_2$/methanol/ 0.1% diethylamine. Fractions containing product were concentrated under reduced pressure and the residue obtained was dissolved in diethyl ether. Hydrogen chloride (1 ml of a 1M solution in diethyl ether) was added dropwise and the resulting solid was triturated under diethyl ether and then dried in vacuo to leave the title compound as a white solid (0.020 g).

Melting point: 144–147° C.
MS (APCI+ve) 391 (M+H)[30] for free base
$^1$H NMR (DMSO-d$_6$) δ 10.33 (1H, s), 8.33 (1H, t), 7.44-6.99 (3H, m), 4.38 (2H, t), 3.50 (2H, d), 2.90 (2H, m), 2.81 (6H, d), 1.95 (3H, s), 1.66 (3H, d), 1.59 (3H, d), 1.50 (6H, d)

EXAMPLE 61

2,5-Dichloro-N-(tricyclo[3.3.1.1$^{3,7}$]dec-1-ylmethyl)-benzamide

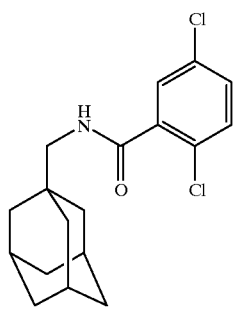

Prepared according to the method described in Example 22 from 2,5-dichlorobenzoic acid (0.319 g), 1-adamantanemethylamine (0.25 g), 4-dimethylaminopyridine (0.204 g) and 1-(3-dimethylaminopropyl)-3-ethylcarbodiimide hydrochloride (0.321 g) in dichloromethane (30 ml). The crude product was purified by silica gel chromatography eluting with dichloromethane to give the title compound as a white solid (0.43 g).

Melting point: 161–162° C.
MS (APCI+ve) 338/340 (M+H)[30]
$^1$HNMR (CDCl$_3$) δ 7.68(1H, d); 7.36-7.30(2H, m); 6.23 (1H$_7$ s); 3.17(2H, d); 2.01(3H, s); 1.76-1.60(6H, m); 1.58 (6H, s).

EXAMPLE 62

2-Chloro-5-methylamino-N-(tricyclo[3.3.1.1$^{3,7}$]dec-1-ylmethyl)-benzamide

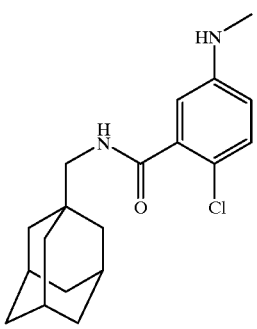

Amino amide from Example 55 (0.12 g) was dissolved in triethylorthoformate (1.07 ml) and heated at 120° C. for three hours. The triethylorthoformate was removed by vacuum distillation. The residue was dissolved in ethanol (5 ml). The solution was cooled to 0° C. under nitrogen, sodium borohydride (0.104 g) was added and the mixture refluxed for three hours at 90° C. The ethanol was removed under reduced pressure, water (20 ml) was added to the residue, the product was extracted into ethyl acetate (3×50 ml), dried over magnesium sulphate and concentrated under reduced pressure. The crude product was purified by silica gel chromatography eluting with dichloromethane:ethyl acetate (1:1) to give the title compound as a white solid (0.04 g).

Melting point: 163–164° C.

MS (APCI+ve) 333/335 (M+H)[30]

$^1$H NMR (CDCl$_3$) δ 7.17(1H, d); 6.96(1H, d); 6.57(1H, dd); 6.35(1H, s); 3.84(1H, s); 3.16(2H, d); 3.83(3H, d); 2.0(3H, s);1.75-1.62(6H, m); 1.6(6H, d).

EXAMPLE 63

2-Chloro-5-(2-chloroethyl)amino-N-(tricylo[3.3.1.1$^{3,7}$]dec-1-ylmethyl)-benzamide

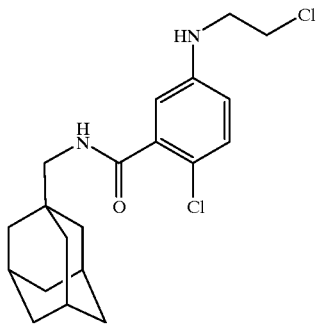

Chloroacetaldehyde (50% solution in water) (0.705 ml) was added to a solution of amino amide from Example 55 (1.5 g) in methanol (15 ml). After 10 minutes hydrochloric acid (0.77 ml of a 50% solution in methanol) was added. Solid sodiumcyanoborohydride (0.317 g) was added and the mixture stirred at ambient temperature for two days. The solvent was removed under reduced pressure, the residue was dissolved in dichloromethane (50 ml) and washed with aqueous sodium hydrogen carbonate (3×50 ml). The organic extracts were dried over magnesium sulphate, filtered and concentrated under reduced pressure. The crude product was purified by silica gel chromatography eluting with hexane:diethylether (1:1) to give the title compound as a yellow solid (1.13 g).

Melting point: 144–145° C.

MS (APCI+ve) 381/383 (M+H)[30]

$^1$H NMR (CDCl$_3$) δ 7.19(1H, d); 7.0(1H, d); 6.62(1H, dd); 6.37(1H, s); 4.18(1H, t); 3.70(2H, t); 3.54-3.44(2H, m); 3.16(2H, d); 2.0(3H, s);1.71-1.62(6H, m); 1.6(6H, d).

EXAMPLE 64

5-Aziridin-1-yl-2-chloro-N-(tricyclo[3.3.1.1$^{3,7}$]dec-1-yhnethyl)-benzamide

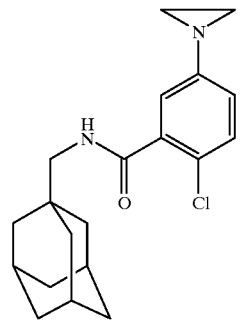

2-Chloro-5-(2-chloroethyl)amino-N-(tricyclo[3.3.1.1$^{3,7}$] dec-1-ylmethyl)-benzamide (0.15 g), cesium carbonate (0.192 g) and acetonitrile (3 ml) were combined and heated in a sealed tube at 100° C. for 24 hours. The cooled reaction mixture was poured into water (50 ml) and the product extracted into ethyl acetate, dried over magnesium sulphate, filtered and concentrated under reduced pressure. The crude product was purified by NPHPLC eluting with 0–5% ethanol in dichloromethane to give the title compound as a white solid (0.023 g).

Melting point: 154–155° C.

MS (APCI+ve) 345/347 (M+H)[30]

$^1$H NMR (CDCl$_3$) δ 8.26(1H, t); 7.30(1H, d); 7.02(1H, dd); 6.95(1H, d); 2.91(2H, d); 2.08(4H, s); 1.94(3H, s); 1.70-1.57(6H, m); 1.51(6H, s).

EXAMPLE 65

2-Methyl-3,5-dinitro-N-(tricyclo[3.3.1 1$^{3,7}$]dec-1-ylmethyl)-benzamide

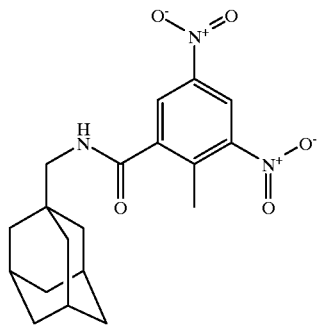

Thionyl chloride (30 ml) was added to 3,5-dinitro-o-toluic acid (6.0 g) and the reaction heated at reflux temperature for 18 hours. The excess thionyl chloride was removed by concentration under reduced pressure and the residue was dissolved in dichloromethane (15 ml). This solution was added to a solution of 1-adamantanemethylamine (2.89 g) in dichloromethane (20 ml) and triethylamine (5 ml) at 0° C. After 10 minutes the reaction mixture was concentrated under reduced pressure and the residue purified by silica gel chromatography eluting with dichloromethane: ethyl acetate (9:1) to give a solid which was further purified by silica gel column chromatography eluting with dichloromethane to give a solid (6.34 g). Part of this material was treated with charcoal in boiling ethyl acetate, filtered and concentrated to remove coloured impurities. Washing the product with ether gave the title compound as a colourless solid.

Melting point: 171–172° C.

MS (APCI+ve) 374 (M+H)+

$^1$H NMR (CDCl$_3$) δ 8.71 (1H, d), 8.39 (1H, d), 5.9-5.8 (1H, m), 3.21 (2H, d), 2.67 (3H, s), 2.04 (3H, s), 1.8-1.7 (3H, m), 1.7-1.6 (3H, m), 1.6-1.55 (6H, m).

EXAMPLE 66

3,5-Diamino-2-methyl-N-(tricyclo[3.3.1.1$^{3,7}$]dec-1-ylmethyl)-benzamide

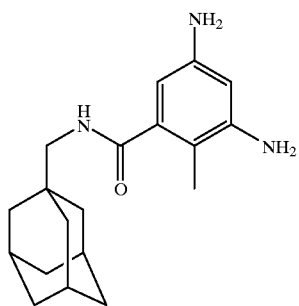

A solution of 2-methyl-3,5-dinitro-N-(tricyclo[3.3.1.1$^{3,7}$]dec-1-ylmethyl)-benzamide (Example 65) (2.66 g) in ethyl acetate (200 ml) was hydrogenated over palladium on carbon (10%, 0.5 g) for 72 hours. The reaction mixture was then filtered through celite® and the residue washed with ethyl acetate. The filtrate and washings were combined and concentrated under reduced pressure to give a solid (0.8 g). This was purified by column chromatography over silica eluting with dichloromethane: ethanol (9:1). The product was further purified by treatment with charcoal in boiling ethanol followed by filtration and concentration to remove coloured impurities to give the title compound as a near colourless solid (0.58 g).

Melting point: 220° C. (dec.)

MS (APCI+ve) 314 (M+H)$^{30}$ $^1$H NMR (DMSO-d$_6$) δ 7.78 (1H, t), 5.93 (1H, d), 5.83 (1H, d), 4.62 (4H, bs), 2.86 (2H, d), 1.93 (3H, s), 1.86 (3H, s), 1.7-1.6 (3H, m), 1.6-1.5 (3H, m), 1.48 (6H, d).

EXAMPLE 67

3,5-Dimethoxy-2-methyl-N-(tricyclo[3.3.1.1$^{3,7}$]dec-1-ylmethyl)-benzamide

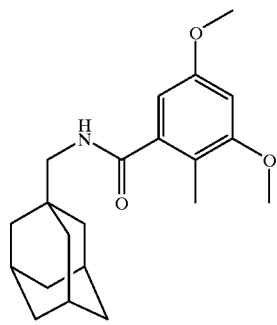

a) 3,5-Dimethoxy-2-methylbenzoic acid

Solid methyl 3,5-dimethoxy-2-methylbenzoate (5.83 g, J. C. S. Perkin I, 1973, 2853.) was dissolved in methanol (80 ml). A solution of aqueous sodium hydroxide (10%, 80 ml) was added and the solution stirred at room temperature for 1 hour. The reaction was then concentrated under reduced pressure to approximately half of the original volume before adding aqueous hydrochloric acid (200 ml). The white precipitate that formed was extracted with ethyl acetate (2×250 ml). The combined extracts were dried over anhydrous magnesium sulphate, filtered and concentrated under reduced pressure to give the sub-title compound as a colourless solid (5.41 g).

$^1$H NMR (CDCl$_3$) δ 7.10 (I1H, d), 6.64 (1H, d), 3.84 (6H, s), 2.45 (3H, s).

b) 3,5-Dimethoxy-2-methyl-N-(tricyclo[3.3.1.1$^{3,7}$] dec-1-ylmethyl)-benzamide A mixture of 3,5-dimethoxy-2-methylbenzoic acid (0.15 g, part a) and thionyl chloride (2 ml) was heated at reflux for 2 minutes and then cooled to room temperature. The excess thionyl chloride was removed by concentration under reduced pressure and the residue dissolved in dichloromethane (1 ml). This solution was added to a solution of 1-adamantanemethylamine (0.188 g) in dichloromethane (5 ml) and triethylamine(1 ml) and the resulting reaction mixture stirred overnight. The reaction was partitioned between dichloromethane (100 ml) and aqueous hydrochloric acid (1M, 50 ml). The organic phase was washed with a saturated aqueous solution of sodium hydrogen carbonate (50 ml), dried over anhydrous magnesium sulphate , filtered and concentrated under reduced pressure to give a colourless solid (0.140 g). This was purified by HPLC over a Dynamax® column eluting with iso-hexane: ethyl acetate (4:1) to give the title compound as a colourless solid (0.110 g).

Melting point: 173–175° C.

MS (APCI+ve) 344 (M+H)$^{30}$ $^1$H NMR (DMSO-d$_6$) δ 8.06 (1H, t), 6.57 (1H, d), 6.41 (1H, d), 3.78 (3H, s), 3.75 (3H, s), 2.91 (2H, d), 2.05 (3H, s), 1.94 (3H, s) 1.75-1.5 (6H, m), 1.49 (6H, d).

EXAMPLE 68

3,5-Dimethoxy-N-(tricyclo[3.3.1.1$^{3,7}$]dec-1-ylmethyl)-benzamide

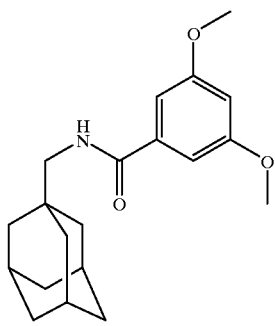

A mixture of 3,5-dimethoxybenzoic acid (0.526 g) and thionyl chloride (5 ml) was heated at reflux for 2 minutes and then cooled to room temperature. The excess thionyl chloride was removed by concentration under reduced pressure and the residue dissolved in dichloromethane (5 ml). This solution was added to a solution of 1-adamantanemethylamine (0.336 g) in dichloromethane (10 ml) and triethylanrine(2 ml) at 0° C. and the resulting reaction mixture stirred for 4 days. The reaction was diluted with dichloromethane (100 ml), washed with aqueous hydrochloric acid (2M, 50 ml) and then washed with a saturated aqueous solution of sodium hydrogen carbonate (50 ml). The organic phase was dried over anhydrous magnesium sulphate, filtered and concentrated under reduced pressure. The residue was purified by column chromatography over silica eluting with dichloromethane: ethyl acetate (19:1) to give the title compound as a colourless solid (0.600 g).

Melting point: 130–133° C.
MS (APCI+ve) 330 (M+H)$^{30}$
$^1$H NMR (DMSO-d$_6$) δ 8.24 (1H, t), 7.01 (2H, d), 6.30 (1H, t), 3.78 (6H, s), 2.97 (2H, d), 1.91 (3H, s), 1.7-1.5 (6H, m), 1.48 (6H, d)

EXAMPLE 69

5-(N-(2-Hydroxy-2-phenylethyl)-2-aminoethyl) amino-2-chloro-N-(tricyclo[3.3.1.1$^{3,7}$]dec-1-ylmethyl)-benzamide

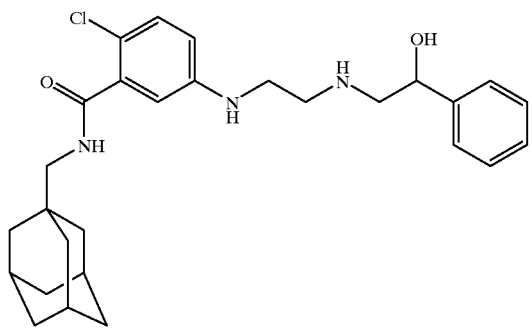

2-Chloro-5-(2-chloroethyl)amino-N-(tricyclo[3.3.1.1$^{3,7}$] dec-1-ylmethyl)benzamide from Example 63 (0.1 g), 2-amino-1-phenylethanol (0.539 g) and triethylamine (0.5 ml) were dissolved in tetrahydrofuran (3 ml) and heated at 80° C. for 60 hours in a sealed tube. The reaction mixture was concentrated under reduced pressure, the residue was suspended in aqueous sodium hydrogen carbonate (30 ml), the product was extracted into ethyl acetate (3×30 ml), dried over magnesium sulphate filtered and concentrated under reduced pressure. Purification by NPHPLC eluting with 0 to 25% ethanol in dichloromethane gave title compound as a white solid (0.044 g).

Melting point: 63–64° C.

MS (APCI+ve) 482/484 (M +H)$^{30}$ $^1$H NMR (CDCl$_3$) δ 7.34(4H, d); 7.307.25(1H, m); 7.13 (1H, d);6.94(1H, d); 7.56(1H, dd); 6.39(1H, t); 4.73(1H, dd); 4.30(1H, s); 3.19-3.14(4H, m); 2.93-2.83(3H, m); 2.80-2.75 (1H, m); 2.0(3H, s); 1.76-1.62(6H, m); 1.57(6H, m).

EXAMPLE 70

2-Chloro-5-(2-(piperidin-1-yl)ethylamino)-N-(tricyclo[3.3.1.1$^{3,7}$]dec-1-ylmethyl)-benzamide, hydrochloride

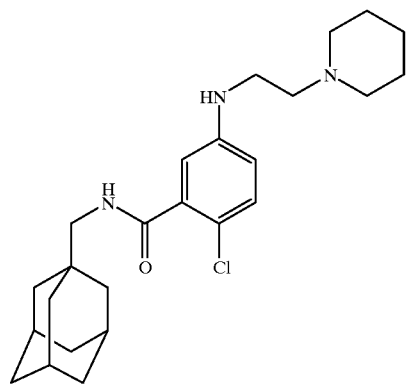

Prepared according to the method described in Example 69 from 2-chloro-5-(2-chloroethyl)amino-N-(tricyclo [3.3.1.1$^{3,7}$]dec-1-ylmethyl)benzamide (0.1 g), piperidine (1 ml),triethylamine (0.5 ml) and tetrahydrofuran (3 ml). Purification by silica gel chromatography eluting with 5% methanol and 1% triethylamine in dichloromethane gave 2-chloro-5-(2-(piperidin-1-yl)ethylamino)-N-(tricyclo [3.3.1.1$^{3,7}$]dec-1-ylmethyl)-benzamide as a glass. Conversion to the hydrochloride salt upon treatment with excess ethereal hydrochloric acid (2M) gave the title compound as a yellow solid (0.062 g).

Melting point: 142–143° C. (Decomposed)

MS (APCI+ve) 430/432 (M+H)$^{30}$ as free base $^1$H NMR (DMSO-d$_6$) δ 8.18(1H, t); 7.17(1H, d); 6.68 (LH, dd); 6.62(1H, d); 3.48-3.45(4H, m); 3.16(2H, s); 2.90 (4H, d); 2.50(4H, s); 1.95(3H, s); 1.80(3H, s); 1.75-1.55(6H, m); 1.52(6H, s).

EXAMPLE 71

5-(N-(2-Hydroxyethyl)-2-aminoethyl)amino-2-chloro-N-(tricyclo[3.3.1.1$^{3,7}$]dec-1-ylmethyl)-benzamide, dihydrochloride

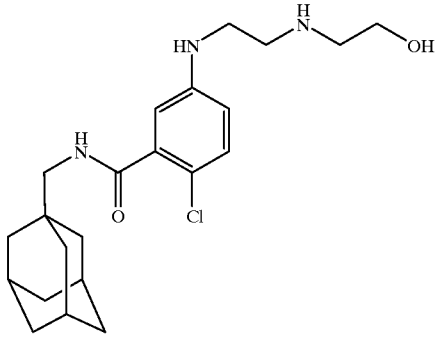

Prepared according to the method described in Example 69 from 2-chloro-5-(2-chloroethyl)amino-N-(tricyclo[3.3.1.1$^{3,7}$]dec-1-ylmethyl)-benzamide (0.1 g), ethanolamine (0.24 g), triethylamine (0.5 ml) and tetrahydrofuran (3 ml). Purification by flash column chromatography eluting with 10% methanol and 1% triethylamine in dichloromethane gave 2-chloro-5-(2-(piperidin-1-yl)ethylamino)-N-(tricyclo[3.3.1.1$^{3,7}$]dec-1 -ylmethyl)-benzamide as a glass. Conversion to the hydrochloride salt upon treatment with excess ethereal hydrochloric acid (2M) gave the title compound as a cream solid (0.056 g).

Melting point: 143° C. (Decomposed)

MS (APCI+ve) 406/408 (M–(hydrochloric acid)+H)$^{30}$ $^1$H NMR (DMSO-d$_6$) δ 8.94(1H, s); 8.19(1H, t); 7.17(1H, dd); 6.67(1H, dd); 6.1 1(1H, d); 3.68(2H, t); 3.43-3.37(2H, m); 3.08-3.03(4H, m); 2.90(2H, d); 1.94(3H, s); 1.69-1.61 (6H, m), 1.52(6H, d).

EXAMPLE 72

2-Chloro-N-(2-[tricyclo[3.3.1.1$^{3,7}$]dec-1-yl]ethyl)-benzamide

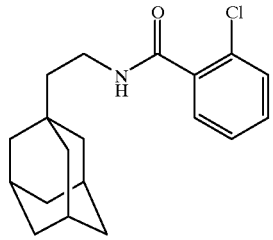

Prepared according to the method of Example 1 from 1-adamantaneethylamine hydrochloride (0.055 g) and 2-chlorobenzoyl chloride (0.033 ml) to give the title compound as a white solid (0.074 g).

Melting point: 125–127° C.

MS (APCI+ve) 318/320 (M+H)$^+$ $^1$H NMR (DMSO-d$_6$) δ 8.31 (1H, t), 7.49-7.33 (4H, m), 3.22 (2H, m), 1.93 (3H, s), 1.70-1.60 (6H, m), 1.51 (6H, d), 1.31 (2H, m).

EXAMPLE 73

2,3-Dichloro-N-(2-[tricyclo[3.3.1.1$^{3,7}$]dec-1-yl] ethyl)-benzamide

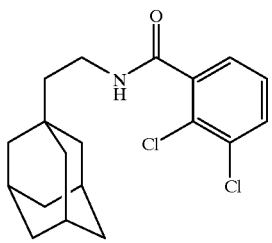

Prepared according to the method of Example 1 from 1-adamantaneethylamine hydrochloride (0.102 g) and 2,3-dichlorobenzoyl chloride (0.102 g) to give the title compound as a white solid (0.090 g).

Melting point: 158–159° C.

MS (APCI+ve) 352/354 (M+H)$^{30}$ $^1$H NMR (DMSO-d$_6$) δ 8.42 (1H, t), 7.68 (1H, dd), 7.40 (1H, t), 7.34 (1H, dd), 3.22 (2H, m), 1.93 (3H, s), 1.64 (6H, m), 1.51 (6H, d), 1.31 (2H, m).

EXAMPLE 74

5-Amino-2-chloro-N-(2-[tricyclo[3.3.1.1$^{3,7}$]dec-1-yl] ethyl)-benzamide

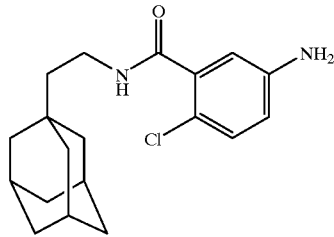

Prepared according to the method of Example 14 from 1-adamantaneethylamine hydrochloride (0.105 g) and 5-amino-2-chlorobenzoic acid (0.132 g) and purified by supercritical fluid chromatography eluting with CO$_2$ in ethanol to give the title compound as a white foam (0.094 g).

Melting point: 147–149° C.

MS (APCI+ve) 333/335 (M+H)$^{30}$ $^1$H NMR (DMSO-d$_6$) δ 8.13 (1H, t), 7.03 (1H, d), 6.56-6.52 (2H, m), 5.36 (2H, s), 3.19 (2H, m), 1.93 (3H, s), 1.66-1.59 (6H, m), 1.50 (6H, d), 1.28 (2H, m).

EXAMPLE 75

2,5-Dimiethyl-N-(2-[tricyclo[3.3.1.1$^{3,7}$]dec-1-yl]ethyl)-benzamide

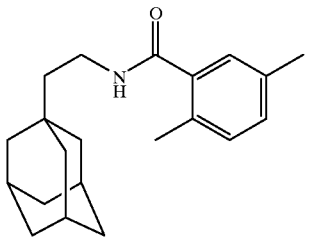

Prepared according to the method of Example 14 from 1-adamantaneethylamine hydrochloride (0.131 g) and 2,5-dimethylbenzoic acid (0.099 g) to give the title compound as a white solid (0.163 g).

Melting point: 153° C.

MS (APCI+ve) 312 (M+H)[30]

$^1$H NMR (DMSO-d$_6$) δ 8.07 (1H, t), 7.10 (3H, m), 3.21 (2H, m), 2.26 (3H, s), 2.25 (3H, s), 1.93 (3H, s), 1.67 (3H, d), 1.62 (3H, d), 1.51 (6H, d), 1.25 (2H, m).

EXAMPLE 76

2-Chloro-N-(3-chloro-tricylo[3.3.1.1$^{3,7}$]dec-1-ylmethyl)-benzamide

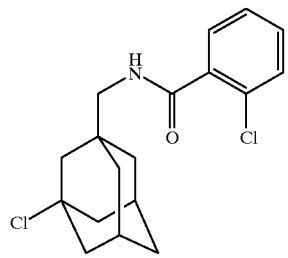

Prepared according to the method of Example 1 from 3-chloro-tricyclo[3.3.1.1$^{3,7}$]decane-1-methanamine, hydrochloride (0.061 g) and 2-chlorobenzoyl chloride (0.0.32 ml) to give the title compound as a white solid (0.093 g).

Melting point: 153° C.

MS (APCI+ve) 3381340/342 (M+H)[30]

$^1$H NMR (DMSO-d$_6$) δ 8.43 (1H, t), 7.51-7.36 (4H, m), 3.02 (2H, d), 2.17 (2H, s), 2.03 (4H, dt), 1.97 (2H, s), 1.64-1.36 (6H, m).

EXAMPLE 77

2-Chloro-3-(N-(2-[imidazoyl-4-yl]ethyl)-2-aminoethyl)amino-N-(tricyclo[3.3.1.1$^{3,7}$]dec-1-ylmethyl)-benzamide

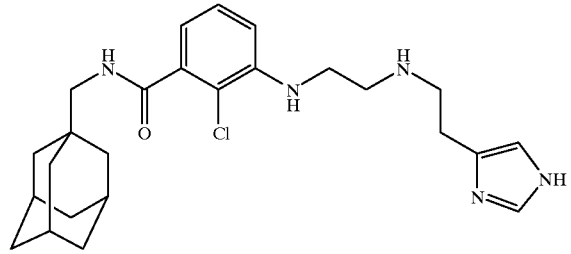

a) 2-Chloro-3-(2-chloroethyl)amino-N-(tricyclo[3.3.1.1$^{3,7}$]dec-1-ylmethyl)-benzamide Prepared according to the method described in Example 63 from 3-amino-2-chloro-N-(tricyclo[3.3.1.$^{3,7}$]dec-1-yl)methylbenzamide from Example 54 (0.7 g), 50% chloroacetaldehyde in water (0.353 ml), sodium cyanoborohydride (0.159 g), 50% hydrochloric acid in methanol (0.385 ml) and methanol (10 ml), giving the subtitled compound as a white solid (0.777 g) after purification by flash column chromatography eluting with 3:1 iso-hexane: ethylacetate.

Melting point: Decomposed 179–180° C.

MS (APCI+ve) 381/383 (M+H)[30]

$^1$H NMR (CDCl$_3$) δ 7.18(1H, t); 6.89(1H, dd); 6.70(1H, dd); 5.88(1H, bs); 4.88(1H, t); 3.75-3.70(2H, m); 3.61-3.55 (2H, m); 3.15(2H, d); 2.02(2H, bs); 1.71-1.62(5H, m); 1.58(5H, d); 1.55(2H, s).

b) 2-Chloro-3-(N-(2-[imidazoyl-4yl]ethyl)-2-aminoethyl)amino-N-(tricyclo[3.3.1.1$^{3,7}$]dec-1-ylmethyl)-benzamide Aminoethylchloride from step a) (0.15 g), histamine (0.437 g), triethylamine (0.5 ml) and tetrahydrofuran were combined and heated in a sealed tube for 60 hours at 80° C. The solvent was removed under reduced pressure, aqueous sodium hydrogencarbonate (30 ml) was added to the residue which was extracted with ethylacetate (3×30 ml). The combined organic extracts were dried over anhydrous magnesium sulphate and concentrated under reduced pressure. The crude product was purified by reverse phase HPLC eluting with 85% to 15% of 0.1% aqueous trifluoroacetic acid in methanol to give the title compound as a white foam (0.07 g).

Melting point: 86–87° C.

MS (APCI+ve) 456/458 (M+H)[30]

$^1$H NMR (CDCl$_3$) δ 7.61(1H, s); 7.17(1H, t); 6.79-6.72 (2H, m); 6.31(1H, s); 6.02(1H, t); 4.76(1H, t); 3.45-3.30(2H, m); 3.17(2H, d); 2.95-2.85(4H, m); 2.75(2H, t); 2.02(3H, s); 1.80-1.60(6H, m); 1.58(6H, d).

EXAMPLE 78

2,5-Dimethyl-N-(3-chloro-tricyclo[3.3.1.1$^{3,7}$]dec-1-ylmethyl)-benzamide

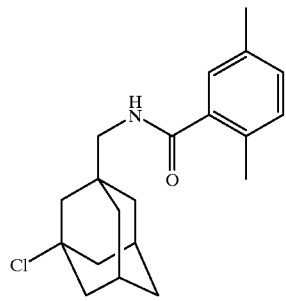

To a suspension of 2,5-dimethylbenzoic acid (0.073 g) in dichloromethane (5 ml) was added oxalyl chloride (0.5 ml) and resulting reaction mixture heated to reflux temperature for 1 hr. Reaction mixture concentrated at reduced pressure and residue dissolved in dichloromethane (5 ml). To this solution was added 3-chloro-tricyclo[3.3.1.1$^{3,7}$]decane-1-methanamine, hydrochloride (0.113 g) and triethylamine (0.30 ml) and reaction mixture stirred at room temperature for 3 hrs before being diluted with diethyl ether and washed with dilute hydrochloric acid followed by sodium hydrogencarbonate solution and then brine. The organic phase was subsequently dried over sodium sulphate (Na$_2$SO$_4$) and concentrated under reduced pressure and further purified by HPLC eluting with 0–5% ethanol in dichloromethane to give the title compound as a white solid (0.068 g).

Melting point: 155° C.

MS (APCI+ve) 332/334/336 (M+H)$^{30}$ $^1$H NMR (DMSO-d$_6$) δ 8.18 (1H, t), 7.10 (3H, s), 3.01 (2H, d), 2.29 (3H, s), 2.28 (3H, s), 2.17 (2H, s), 2.03 (4H, m), 1.90 (2H, s), 1.64-1.41 (6H, m).

EXAMPLE 79

3,5-Dimethoxy-2-methyl-N-(3-chloro-tricyclo[3.3.1.1$^{3,7}$]dec-1ylmethyl)-benzamide

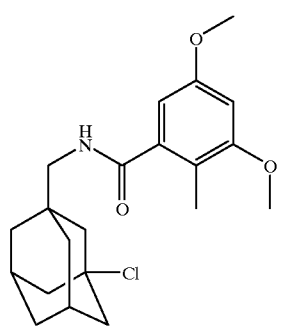

A mixture of 3,5-dimethoxy-2-methylbenzoic acid from Example 67 a) (0.15 g) and thionyl chloride (2 ml) was heated to reflux temperature for 2 minutes before cooling to room temperature and concentratedunder reduced pressure. The residue was dissolved in dichloromethane (1 ml) and added to a solution of 1-adamantanemethylamine (0.104 g) in dichloromethane (5 ml) and triethylamine (1 ml) and the resulting reaction mixture stirred for 2 days. The reaction was partitioned between dichloromethane (100 ml) and aqueous hydrochloric acid (0.5M, 50 ml). The organic phase was washed with a saturated aqueous solution of sodium hydrogen carbonate (50 ml), dried over anhydrous magnesium sulphate, filtered and concentrated under reduced pressure. The residue was purified by HPLC over a Dynamax® column eluting with iso-hexane: ethyl acetate (4:1) to give the title compound as a colourless solid (0.090 g).

Melting point: 173–175° C.

MS (APCI+ve) 378 (M+H)$^{30}$ $^1$H NMR (DMSO-d$_6$) δ 8.17 (1H, t), 6.58 (1H, d), 6.43 (1H, d), 3.79 (3H, s), 3.76 (3H, s), 3.00 (2H, d), 2.16 (2H, s), 2.1-1.95(4H, m), 2.05 (3H, s), 1.89 (2H, s) 1.7-1.5 (6H, m).

EXAMPLE 80

2-Chloro-5-iodo-N-(tricyclo[3.3.1.1$^{3,7}$]dec-1-ylmethyl)-benzamide

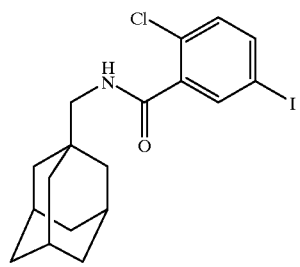

To a solution of amino amide from Example 55 (200 mg) in 75% aqueous tetrahydrofuran 1/3 (10 ml) at −5 C. was added sulphuric acid (0.2 ml) followed by sodium nitrite (0.042 g) in water (1 ml). The resulting reaction mixture was stirred for 40 min before potassium iodide (0.136 g) was added. The reaction mixture was heated at 90 C. for 1 hour, cooled to room temperature and diluted with water and extracted with ethyl acetate. The organic layers were separated and dried over magnesium sulphate. The filtered solution was concentrated under reduced pressure and the crude material purified over silica eluting with hexaneslethyl acetate to give the title compound as a white solid (0.23 g).

Melting point: 161.4–161.5° C.

MS (APCI+ve) 430 (M+H)$^{30}$ ;

$^1$H NMR (CDCl$_3$) δ 7.99 (1H, d), 7.66 (1H, dd), 7.13 (1H, d), 6.18 (1H, bs), 3.16(2H, d), 2.01 (3H, bs), 1.73 (3H, d), 1.65 (3H, d), 1.57 (6H, bs).

EXAMPLE 81

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of Examples 1 to 80 were tested for antagonist activity at the P2X$_7$ receptor. Thus, the test was performed in 96-well flat bottomed microtitre plates, the wells being filled with 250 μl of test solution comprising 200 μl of a suspension of THP-1 cells (2.5×10$^6$ cells/ml) containing 10$^{-4}$M ethidium bromide, 25 μl of a high potassium buffer solution containing 10$^{-5}$M bbATP, and 25 μl of the high potassium buffer solution containing 3×10$^{-5}$M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of Examples 1 to 80 demonstrated antagonist activity, having a pIC$_{50}$ figure>4.50.

What is claimed is:

1. A compound of general formula

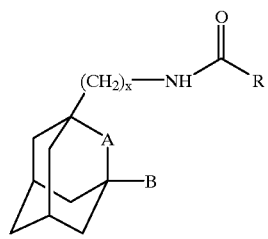

(I)

wherein x represents 1 or 2; A represents a group CH$_2$;

B represents a hydrogen or halogen atom;

R represents a phenyl, pyridyl, indolyl, indazolyl, pyrimidinyl or thiophenyl group, each of which may be optionally substituted by one or more substituents independently selected from the group consisting of a halogen atom, an amino, cyano, hydroxyl, nitro, C$_1$–C$_6$-alkyl, halo-C$_1$–C$_6$-alkyl, —N(R$^1$)—C(=O)—R$^2$, —NR$^5$R$^6$, C$_3$–C$_8$-cycloalkyl, 3- to 8-membered heterocyclyl, C$_3$–C$_8$-cycloalkyloxy, C$_1$–C$_6$-alkylcarbonyl, C$_1$–C$_6$-alkylsulphinyl or C$_1$–C$_6$-alkylsulphonyl group, or a C$_1$–C$_6$-alkoxy, C$_1$–C$_6$-alkylamino, phenoxy, benzyl, C$_1$–C$_6$-alkylthio and phenylthio group optionally substituted by one or more substituents independently selected from the group consisting of a halogen atom, an amino, cyano, carboxyl, hydroxyl, nitro, 1-pyrrolidinyl, 1-piperidinyl, C$_1$–C$_6$-alkyl, C$_1$–C$_6$-alkoxy, (di)C$_1$–C$_6$-alkylamino, halo-C$_1$–C$_6$-alkyl, C$_1$–C$_6$-alkoxycarbonyl or one of the following groups:

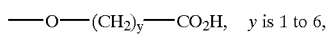

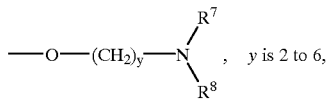

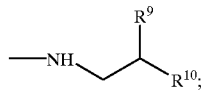

R$^1$ represents a hydrogen atom or a C$_1$–C$_6$-alkyl or C$_3$–C$_8$-cycloalkyl group;

R$^2$ represents a C$_1$–C$_6$-alkyl or C$_3$–C$_8$-cycloalkyl group;

R$^5$ represents a hydrogen atom or a C$_1$–C$_6$-alkyl or C$_3$–C$_8$-cycloalkyl group;

R$^6$ represents a C$_3$–C$_8$-cycloalkyl group and, additionally, a C$_1$–C$_6$-alkyl group when R$^5$ is not a hydrogen atom;

R$^7$ represents a hydrogen atom or a C$_1$–C$_6$-alkyl or C$_3$–C$_8$-cycloalkyl group;

R$^8$ represents a C$_1$–C$_6$-alkyl or C$_3$–C$_8$-cycloalkyl group;

R$^9$ represents a hydrogen atom or a hydroxyl group; and

R$^{10}$ represents a hydrogen atom or a phenyl or imidazolyl group;

with the proviso that when B represents a hydrogen atom, and R is a phenyl- or pyridyl-containing group, the phenyl or pyridyl moiety is substituted as defined above; or a pharmaceutically acceptable salt or solvate thereof.

2. A compound according to claim 1, wherein R represents a phenyl, pyridyl or indolyl group, each of which may be optionally substituted by one or two substituents independently selected from a fluorine, chlorine, bromine or iodine atom or an amino, hydroxyl, nitro, aziridinyl, pyrrolidinyl, C$_1$–C$_4$-alkyl, trifluoromethyl, —NR$^5$R$^6$, C$_1$–C$_4$-alkylsulphinyl or C$_1$–C$_4$-alkylsulphonyl group, or a C$_1$–C$_4$-alkoxy, C$_1$–C$_4$-alkylamino, benzyl, C$_1$–C$_4$-alkylthio or phenylthio group optionally substituted by one or two substituents independently selected from a halogen atom or an amino, cyano, carboxyl, hydroxyl, 1-pyrrolidinyl, 1-piperidinyl, methyl, methoxy, dimethylamino, C$_1$–C$_4$-alkoxycarbonyl or one of the following groups:

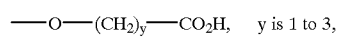

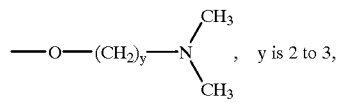

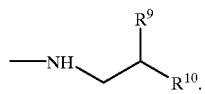

3. A compound according to claim 1, wherein R$^5$ represents a hydrogen atom or a C$_1$–C$_4$-alkyl group.

4. A compound according to claim 1, wherein R$^6$ represents a C$_1$–C$_4$-alkyl group when R is not a hydrogen atom.

5. A compound of formula (I) as defined in claim 1, or a pharmaceutically acceptable salt or solvate thereof, being:

2,4-Dichloro-N-(tricyclo[3.3.1.1$^{3,7}$]dec-1-methyl)-benzamide, 3,5-Dichloro-N-(tricyclo[3.3.1.1$^{3,7}$]dec-1-methyl)-benzamide, 2-Chloro-N-(tricyclo[3.3.1.1$^{3,7}$]dec-1-methyl)-benzamide, 2,6-Dichloro-N-(tricyclo[3.3.1.1$^{3,7}$]dec-1-methyl)-benzamide, 2-Methoxy-N-(tricyclo[3.3.1.1$^{3,7}$]dec-1-methyl)-benzamide, 2-Methyl-N-(tricyclo[3.3.1.1$^{3,7}$]dec-1-methyl)-benzamide, 2-Bromo-N-(tricyclo[3.3.1.1$^{3,7}$]dec-1-methyl)-benzamide,
2-Iodo-N-(tricyclo[3.3.1.1$^{3,7}$]dec-1-methyl)-benzamide,
2-Nitro-N-(tricyclo[3.3.1.1$^{3,7}$]dec-1-methyl)-benzamide,
2,6-Dimethoxy-N-(tricyclo[3.3.1.1$^{3,7}$]dec-1-methyl)-benzamide,
2-(Trifluoromethyl)-N-(tricyclo[3.3.1.1$^{3,7}$]dec-1-methyl)-benzamide,
2,6-Difluoro-N-(tricyclo[3.3.1.1$^{3,7}$]dec-1-methyl)-benzarnide,
2-(Trifluoromethyl)-6-flouro-N-(tricyclo[3.3.1.1$^{3,7}$]dec-1-methyl)-benzamide,
2-Amino-6-chloro-N-(tricyclo[3.3.1.1$^{3,7}$]dec-1-methyl)-benzamide,
2-Chloro4-nitro-N-(tricyclo[3.3.1.1$^{3,7}$]dec-1-methyl)-benzamide,
2-(2-Cyanophenylthio)-N-(tricyclo[3.3.1.1$^{3,7}$]dec-1-methyl)-benzamide,
2-(4-Methylphenylthio)-N-(tricyclo[3.3.1.1$^{3,7}$]dec-1-methyl)-3-pyridine carboxamide,
2-(Methylthio)-N-(tricyclo[3.3.1.1$^{3,7}$]dec-1-methyl)-benzamide,
2-(Methylthio)-N-(tricyclo[3.3.1.1$^{3,7}$]dec-1-methyl)-3-pyridine carboxamide,
3-Chloro-N-(tricyclo[3.3.1.1$^{3,7}$]dec-1-methyl)-benzaride,
2,3-Dichloro-N-(tricyclo[3.3.1.1$^{3,7}$]dec-1-methyl)-benzamide,
2,5-Dimethyl-N-(tricyclo[3.3.1.1$^{3,7}$]dec-1-methyl)-benzamide,
2-(Phenylmethyl)-N-(tricyclo[3.3.1.1$^{3,7}$]dec-1-methyl)-benzamide,
2-(2-(N,N-Dimethylamino)ethyloxy)-N-(tricyclo[3.3.1.1$^{3,7}$]dec-1-methyl)-benzamide, hydrochloride,
2-[[(Tricyclo[3.3.1.1$^{3,7}$]dec-1-ylmethyl)amino]carbonyl]phenyl-1-oxyacetic acid, 1,1-dimethylethyl ester,
2-[[(Tricyclo[3.3.1.1$^{3,7}$]dec-1-ylmethyl)amnino]carbonyl]phenyl-1-oxyacetic acid,
2-(Methylsulphoxide)-N-(tricyclo[3.3.1.1$^{3,7}$]dec-1-methyl)-3-pyridine carboxamide,
N-(tricyclo[3.3.1.1$^{3,7}$]dec-1-methyl)-5-indole carboxamide,
2-Amino-6-chloro-N-(2-[tricyclo[3.3.1.1$^{3,7}$]dec-1-yl]ethyl)benzamide,
2-(2-Methylsulphonyl)-N-(tricyclo[3.3.1.1$^{3,7}$]dec-1-ylmethyl)-3-pyridine carboxamide,
2-(2-Aminoethylthio)-N-(tricyclo[3.3.1.1$^{3,7}$]dec-1-ylmethyl)-3-pyridine carboxamide, trifluoroacetate,
2-(2-(N,N-Dimethylamino)ethylamino)-N-(tricyclo[3.3.1.1$^{3,7}$]dec-1-ylmethyl)-3-pyridine carboxamide, dihydrochloride,
2-(2-(Pyrrolidin-1-ylethylamino)-N-(tricyclo[3.3.1 1$^{3,7}$]dec-1-ylmethyl)-3-pyridine carboxamide, dihydrochloride,
2-(Methylamino)-N-(tricyclo[3.3.1.1$^{3,7}$]dec-1-ylmethyl)-3-pyridine carboxamide, dihydrochloride,
2-(Dimethylamino)-N-(tricyclo[3.3.1.1$^{3,7}$]dec-1-ylmethyl)-3-pyridine carboxamide, hydrochloride,
2-(Pyrrolidin-1-yl)-N-(tricyclo[3.3.1.1$^{3,7}$]dec-1-ylmethyl)-3-pyridine carboxamide, dihydrochloride,
2-(2,5-Dimethoxyphenylthio)-N-(tricyclo[3.3.1.1$^{3,7}$]dec-1-ylmethyl)-3-pyridine carboxamide,
2-Chloro-5-methylthio-N-(tricyclo[3.3.1.1$^{3,7}$]dec-1-ylmethyl)benzamide,
2-(2-(N,N-Dimethylamino)ethylthio)-N-(tricyclo[3.3.1.1$^{3,7}$]dec-1-ylmethyl)benzamide,
2-(4-Methoxyphenylthio)-N-(tricyclo[3.3.1.1$^{3,7}$]dec-1-ylmethyl)-3-pyridine carboxamide,
2-Chloro-3-fluoro-N-(tricyclo[3.3.1.1$^{3,7}$]dec-1-ylmethyl)benzamide,
2-Bromo-5-fluoro-N-(tricyclo[3.3.1.1$^{3,7}$]dec-1-ylmethyl)-benzanide,
2-Chloro-5-fluoro-N-(tricyclo[3.3.1.1$^{3,7}$]dec-1-ylmethyl)-benzamide,
2-(2,5-Dihydroxyphenylthio)-N-(tricyclo[3.3.1.1$^{3,7}$]dec-1-ylmethyl)-3-pyridine carboxamide,
3-[[(Tricyclo[3.3.1.1$^{3,7}$]dec-1-ylmethyl)amino]carbonyl]pyridyl-2-thioacetic acid,
(2-Chloro-6-methyl)-N-(tricyclo[3.3.1.1$^{3,7}$]dec-1-ylmethyl)-3-pyridine carboxamide,
3-[[(Tricyclo[3.3.1.1$^{3,7}$]dec-1-ylmethyl)amino]carbonyl]pyridyl-2-(4phenylthio)oxyacetic acid,
2-(4-(3-N,N-dimethylamino)propyloxyphenylthio)-N-(tricyclo[3.3.1.1$^{3,7}$]dec-1-ylmethyl)-3-pyridine carboxamide, dihydrochloride,
(2-Methylthio-6-methyl)-N-(tricyclo[3.3.1.1$^{3,7}$]dec-1-ylmethyl)-3-pyridine carboxamide,
2-[[(Tricyclo[3.3.1.1$^{3,7}$]dec-1-ylmethyl)arnino]carbonyl]phenyl-1-oxybutyric acid,
2-Chloro-5-hydroxy-N-(tricyclo[3.3.1.1$^{3,7}$]dec-1-ylmethyl)benzamide,
2-Chloro-3-nitro-N-(tricyclo[3.3.1.1$^{3,7}$]dec-1-ylmethyl)benzamide,
2-Chloro-5-nitro-N-(tricyclo[3.3.1.1$^{3,7}$]dec-1-ylmethyl)-benzamide,
3-Amino-2-chloro-N-(tricyclo[3.3.1.1$^{3,7}$]dec-1-ylmethyl)-benzamide,
5-Amino-2-chloro-N-(tricyclo[3.3.1.1$^{3,7}$]dec-1-ylmethyl)benzamide,
2-Chloro-3-(N,N-dimethylamino)ethylamino-N-(tricyclo[3.3.1.1$^{3,7}$]dec-1-ylmethyl)-benzamide,
2-Chloro-5-(N,N-dimethylamino)ethylamino-N-(tricyclo[3.3.1.1$^{3,7}$]dec-1-ylmethyl)-benzamide,
2-Chloro-5-(N,N-dimethylamino)ethylthio-N-(tricyclo[3.3.1.1$^{3,7}$]dec-1 -ylmethyl)-benzamide, fumarate,
2-Chloro-3-hydroxy-N-(tricyclo[3.3.1.1$^{3,7}$]dec-1-ylmethyl)benzamide,
2-Chloro-5-(N,N-dimethylamino)ethyloxy-N-(tricyclo[3.3.1.1$^{3,7}$]dec-1-ylmethyl)-benzamide,
2,5-Dichloro-N-(tricyclo[3.3.1.1$^{3,7}$]dec-1-ylmethyl)benzamide,
2-Chloro-5-methylamino-N-(tricyclo[3.3.1.1$^{3,7}$]dec-1-ylmethyl)benzamide,
2-Chloro-5-(2-chloroethyl)amino-N-(tricyclo[3.3.1.1$^{3,7}$]dec-1-ylmethyl)benzamide,
5-Aziridin-1-yl-2-chloro-N-(tricyclo[3.3.1.1$^{3,7}$]dec-1-ylmethyl)benzamide,
2-Methyl-3,5-dinitro-N-(tricyclo[3.3 1.1$^{3,7}$]dec-1-ylmethyl)-benzamide,
3,5-Diamino-2-methyl-N-(tricyclo[3.3.1.1$^{3,7}$]dec-1-ylmethyl)benzamide,
3,5-Dimethoxy-2-methyl-N-(tricyclo[3.3.1.1$^{3,7}$]dec-1-ylmethyl)-benzamide,
3,5-Dimethoxy-N-(tricyclo[3.3.1.1$^{3,7}$]dec-1-ylmethyl)benzamide,
5-(N-(2-Hydroxy-2-phenylethyl)-2-aminoethyl)amino-2-chloro-N-(tricyclo[3.3.1.1$^{3,7}$]dec-1-ylmethyl)-benzamide,
2-Chloro-5-(2-(piperidin-1-ylethylamino)-N-(tricyclo[3.3.1.1$^{3,7}$]dec-1-ylmethyl)-benzamide, hydrochloride,
5-(N-(2-Hydroxyethyl)-2-aminoethyl)amino-2-chloro-N-(tricyclo[3.3.1.1$^{3,7}$]dec-1-ylmethyl)benzamide, dihydrochloride, 2-Chloro-N-(2-[tricyclo[3.3.1.1$^{3,7}$]dec-1-yl]ethyl)-benzamide, 2,3-Dichloro-N-(2-[tricyclo[3.3.1.1$^{3,7}$]dec-1-yl]ethyl)-benzamide, 5-Amino-2-chloro-N-(2-[tricyclo[3.3.1.1$^{3,7}$]dec-1-yl]ethyl)benzamide, 2,5-Dimethyl-N-(2-[tricyclo[3.3.1.1$^{3,7}$]dec-1-yl]ethyl)-benzamide, 2-Chloro-N-(3chloro-tricyclo[3.3.1.1$^{3,7}$]dec-1-ylmethyl)benzamide, 2-Chloro-3-(N-(2-[imidazoyl4-yl]ethyl)-2-aminoethyl)amino-N-(tricyclo[3.3.1.1$^{3,7}$]dec-1-ylmethyl)-benzamide, 2,5-Dimethyl-N-(3-chloro-tricyclo[3.3.1.1$^{3,7}$]dec-1ylmethyl)benzamide, 3,5-Dimethoxy-2-methyl-N-(3-chloro-tricyclo[3.3.1.1$^{3,7}$]dec-1ylmethyl)benzamide, and 2-Chloro-5-iodo-N-(tricyclo[3.3.1.1$^{3,7}$]dec-1-ylmethyl)-benzamide.

6. A process for the preparation of a compound of formula (I) as defined in claim 1 which comprises reacting a compound of general formula

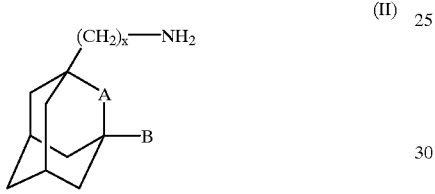

(II)

wherein x, A and B are as defined in formula (I), with a compound of general formula

(III)

wherein R is as defined in formula (I) and L is a leaving group; and optionally forming a pharmaceutically acceptable salt or solvate thereof.

7. A pharmaceutical composition comprising a compound of formula (I), or a pharmaceutically acceptable salt or solvate thereof, as claimed in claim 1 in association with a pharmaceutically acceptable adjuvant, diluent or carrier.

8. A process for the preparation of a pharmaceutical composition as claimed in claim 7 which comprises mixing a pharmaceutically acceptable adjuvant, diluent or carrier with a compound of formula (1)

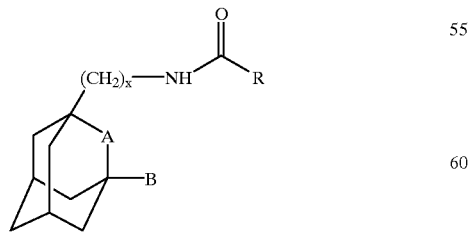

(I)

wherein x represents 1 or 2: A represents a group $CH_2$;

B represents a hydrogen or halogen atom:

R represents a phenyl, pyridyl, indolyl, indazolyl, pyrimidinyl or thiophenyl group, each of which may be optionally substituted by one or more substituents independently selected from the group consisting of a halogen atom, an amino, cyano, hydroxyl, nitro, $C_1$–$C_6$-alkyl. halo-$C_1$–$C_6$-alkyl, —N($R^1$)—C(=O)—$R^2$, —N$R^5R^6$, $C_3$–$C_3$-cycloalkyl, 3- to 8-membered heterocyclyl, $C_3$–$C_8$-cycloalkyloxy, $C_1$–$C_6$-alkylcarbonyl, $C_1$–$C_6$-alkylsulphinyl or $C_1$–$C_6$-alkylsulphonyl group, or a $C_1$–$C_6$-alkoxy, $C_1$–$C_6$-alkylamino, phenoxy, benzyl, $C_1$–$C_6$-alkylthio and phenylthio group optionally substituted by one or more substituents independently selected from the group consisting of a halogen atom, an amino, cyano, carboxyl, hydroxyl, nitro, 1-pyrrolidinyl, 1-piperidinyl, $C_1$–$C_6$-alkyl, $C_1$–$C_6$-alkoxy, (di)$C_1$–$C_6$-alkylamino, halo-$C_1$–$C_6$-alkyl, $C_1$–$C_6$-alkoxycarbonyI or one of the following groups:

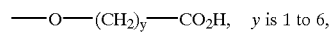

—O—$(CH_2)_y$—$CO_2H$,  y is 1 to 6,

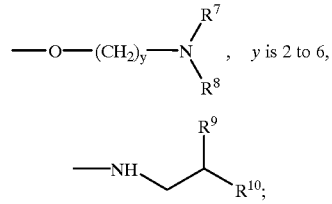

—O—$(CH_2)_y$—N$\begin{smallmatrix}R^7\\R^8\end{smallmatrix}$ ,  y is 2 to 6,

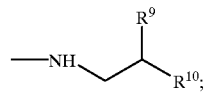

—NH—$\begin{smallmatrix}R^9\\R^{10}\end{smallmatrix}$;

$R^1$ represents a hydrogen atom or a $C_1$–$C_6$-alkyl or $C_3$–$C_8$-cycloalkyl group;

$R^2$ represents a $C_1$–$C_6$-alkyl or $C_3$–$C_8$-cycloalkyl group;

$R^5$ represents a hydrogen atom or a $C_1$–$C_6$-alkyl or $C_3$–$C_8$-cycloalkyl group;

$R^6$ represents a $C_3$–$C_8$-cycloalkyl group and, additionally, a $C_1$–$C_6$-alkyl group when $R^5$ is not a hydrogen atom;

$R^7$ represents a hydrogen atom or a $C_1$–$C_6$-alkyl or $C_3$–$C_8$-cycloalkyl group;

$R^8$ represents a $C_1$–$C_6$-alkyl or $C_3$–$C_8$-cycloalkyl group;

$R^9$ represents a hydrogen atom or a hydroxyl group; and $R^{10}$ represents a hydrogen atom or a phenyl or imidazolyl group;

with the proviso that when B represents a hydrogen atom and R is a phenyl- or pyridyl-containing group, the phenyl or pyridyl moiety is substituted as defined above; or a pharmaceutically acceptable salt or solvate thereof.

9. A method of effecting immunosuppression which comprises administering to a patient a therapeutically effective amount of a compound of formula (I), or a pharmaceutically acceptable salt or solvate thereof, as claimed in claim 1.

* * * * *